(12) United States Patent
Shenouda

(10) Patent No.: US 12,096,922 B1
(45) Date of Patent: Sep. 24, 2024

(54) APPARATUS, METHODS, AND SYSTEMS FOR IMPROVING SURGICAL CONTROL WITH A MEDICAL TORQUING DEVICE

(71) Applicant: Krueze Innovations LLC, Boynton Beach, FL (US)

(72) Inventor: George Shenouda, Boynton Beach, FL (US)

(*) Notice: Subject to any disclaimer, the term of this patent is extended or adjusted under 35 U.S.C. 154(b) by 0 days.

(21) Appl. No.: 18/494,681

(22) Filed: Oct. 25, 2023

(51) Int. Cl.
  *A61B 17/00* (2006.01)
  *A61B 17/28* (2006.01)
(52) U.S. Cl.
  CPC ...... *A61B 17/00234* (2013.01); *A61B 17/282* (2013.01); *A61B 2017/00353* (2013.01); *A61B 2017/00367* (2013.01); *A61B 17/2833* (2013.01)
(58) Field of Classification Search
  CPC ............ A61B 17/00234; A61B 17/282; A61B 17/2833; A61B 2017/00353; A61B 2017/00367
  USPC .......................................................... 606/1
  See application file for complete search history.

(56) References Cited

U.S. PATENT DOCUMENTS

| 5,626,607 A | 5/1997 | Malecki et al. |
| 2010/0010616 A1 | 1/2010 | Drews et al. |
| 2014/0073854 A1 | 3/2014 | Vincent et al. |
| 2014/0114126 A1 | 4/2014 | Dresher |
| 2016/0095510 A1 | 4/2016 | Oskin et al. |
| 2017/0251917 A1 | 9/2017 | Reydel |
| 2019/0290260 A1 | 9/2019 | Caffes et al. |
| 2020/0054192 A1 | 2/2020 | Noyes |
| 2020/0360005 A1 | 11/2020 | Rodriguez Salazar et al. |
| 2021/0235973 A1 | 8/2021 | Gray et al. |

FOREIGN PATENT DOCUMENTS

CN    105232134    *    1/2016

OTHER PUBLICATIONS

Haochen Wang et al., A Hybrid Electromagnetic and Tendon-Driven Actuator for Minimally Invasive Surgery, Actuators, Sep. 21, 2020, p. 92, vol. 9 No. 3, MDPI.

* cited by examiner

*Primary Examiner* — Aaron F Roane
(74) *Attorney, Agent, or Firm* — Derek Fahey, Esq.; The IP Plus Firm, PLLC

(57) ABSTRACT

A medical torquing device for improving surgical control is disclosed. The device features an outer body with a first u-channel, accommodating a semi-tubular shaft that can transition between closed and open configurations. The device further includes an engaging element having a torque-locking mechanism with wheels and teeth, ensures secure locking and controlled movement. The first u-channel includes an elongated slot for receiving a plurality of medical instruments for invasive surgeries and interventional treatments. Additionally, a handle with a second u-channel enhances grip and control and facilitates retention of the medical instruments within the first u-channel. The invention's configuration allows for a portion of the first wheel to extend through an opening in the semi-tubular shaft in the locked configuration.

20 Claims, 14 Drawing Sheets

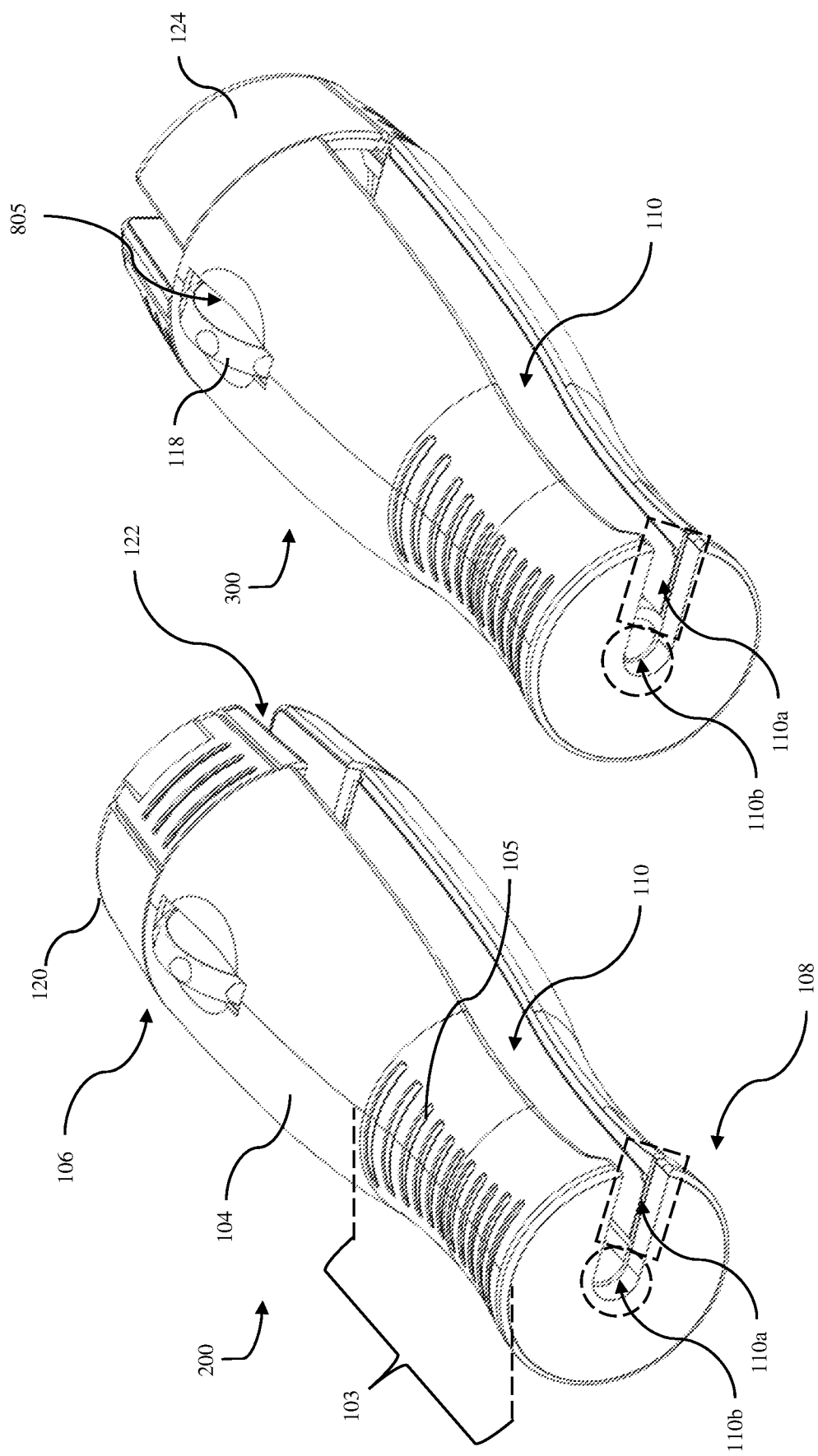

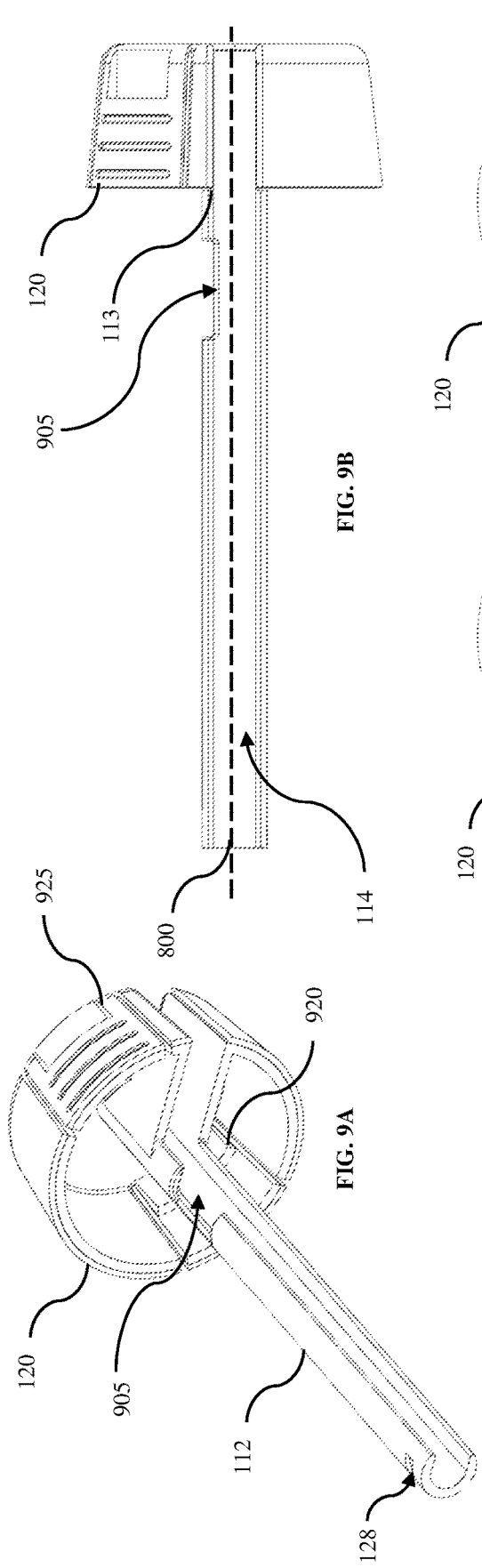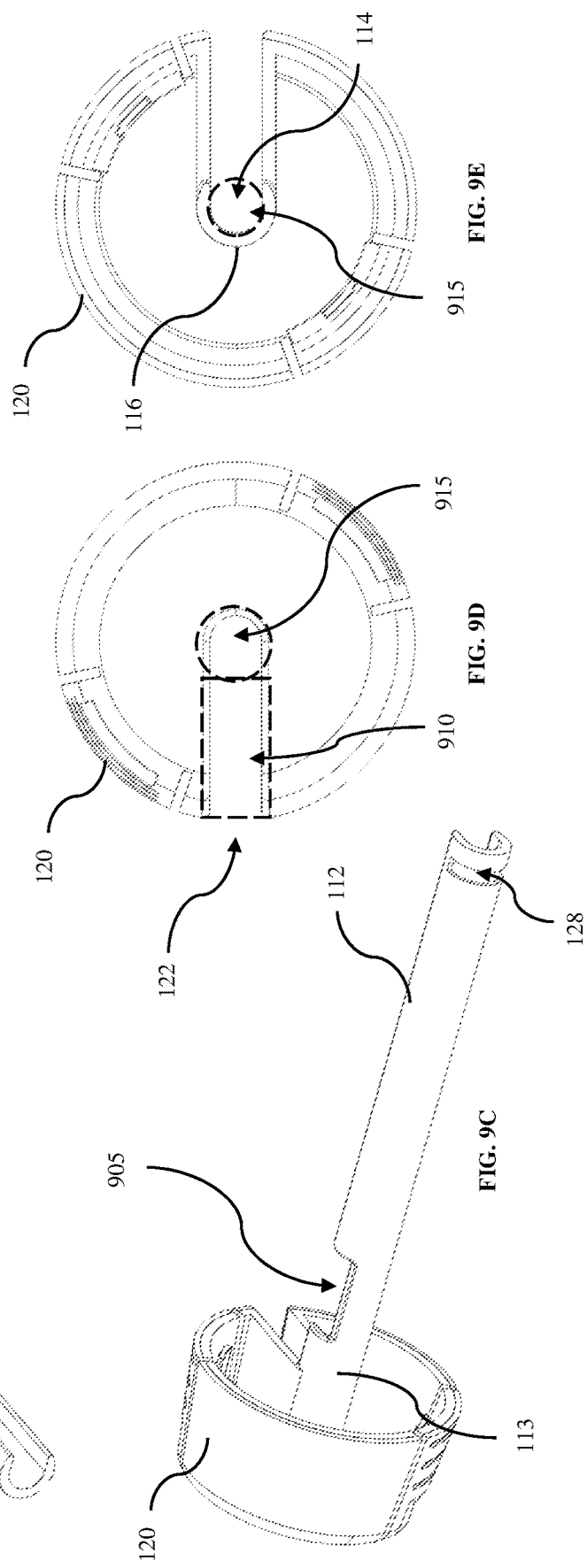

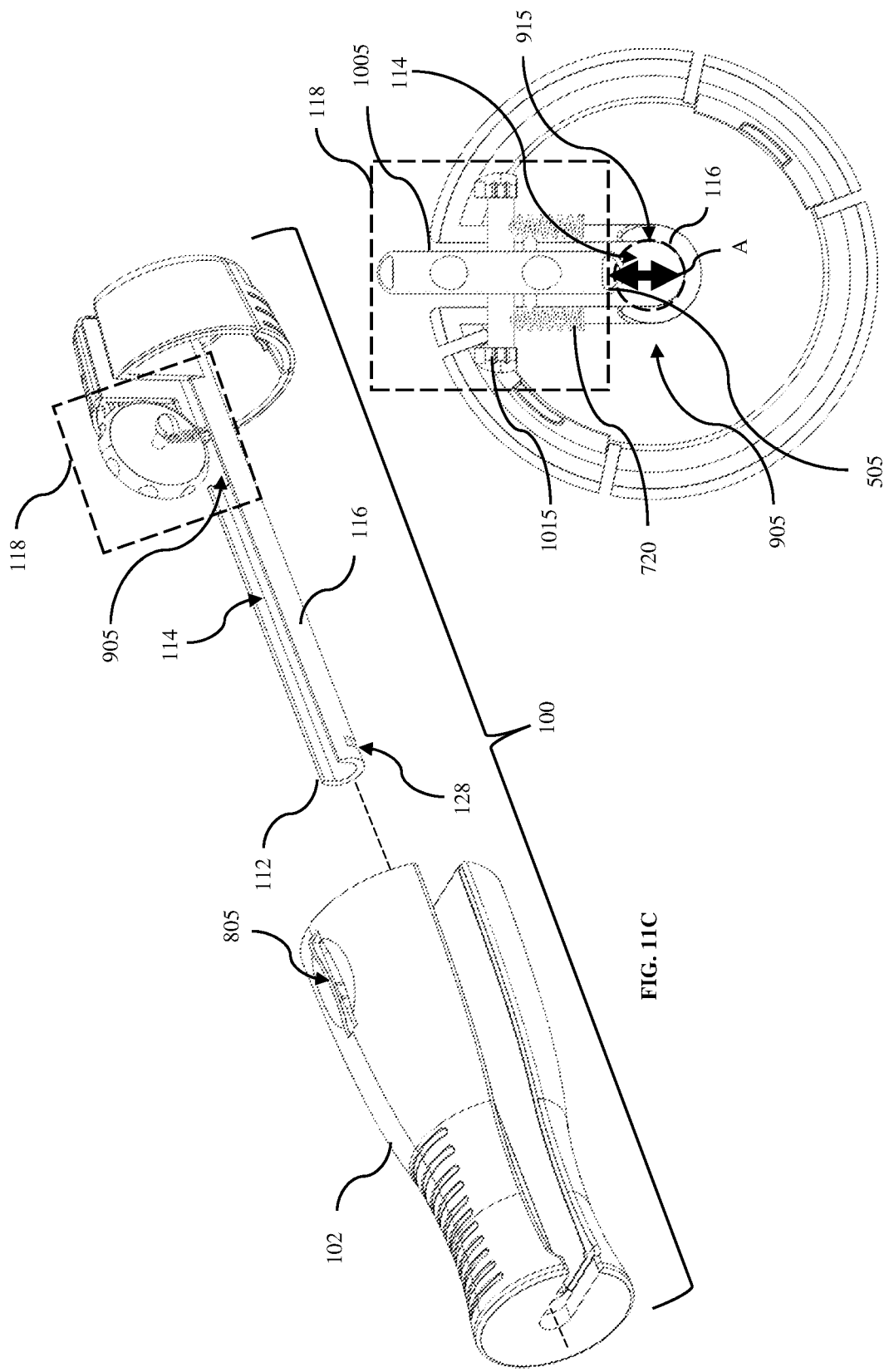

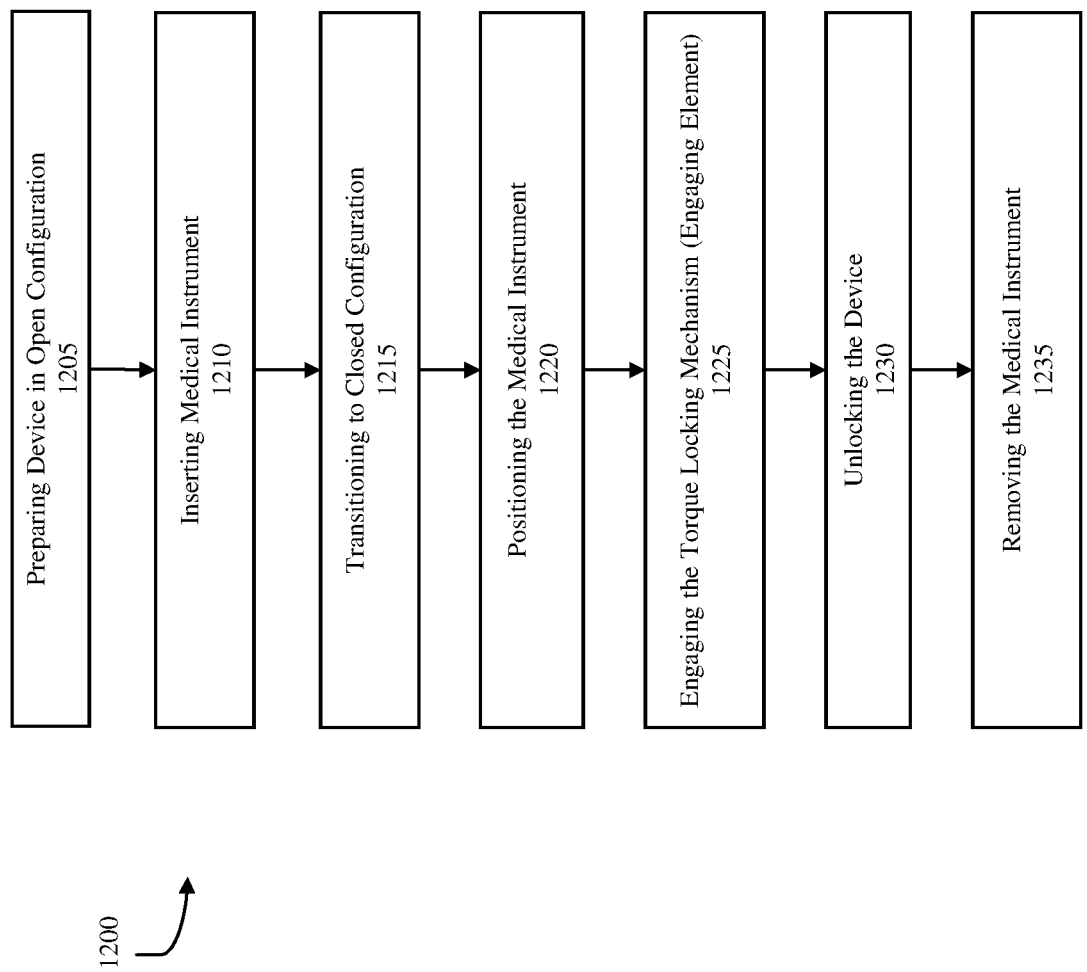

APPARATUS, METHODS, AND SYSTEMS FOR IMPROVING SURGICAL CONTROL WITH A MEDICAL TORQUING DEVICE

REFERENCE TO RELATED APPLICATIONS

Not Applicable.

CROSS-REFERENCES

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISK

Not applicable.

TECHNICAL FIELD

The present disclosure relates to the field of medical devices, and more specifically to the field of medical torquing devices used in minimally invasive surgical procedures and interventional medical treatments.

BACKGROUND OF THE INVENTION

The field of medical torquing devices has witnessed significant advancements in recent years, primarily in response to the growing demand for minimally invasive surgical techniques and improved control during interventional procedures. These devices play a crucial role in enabling precise manipulation and rotation of medical instruments within a patient's body. However, despite these advancements, certain challenges persist within the realm of existing medical torquing devices, necessitating innovation and improvement.

One of the prominent issues with current medical torquing devices is their limited capacity to provide precise control and secure locking mechanisms. Many existing devices exhibit limitations in their capacity to ensure stable instrument positioning within the patient's body. These limitations can lead to difficulties in navigating complex anatomical structures, increasing the risk of procedural complications, and necessitating extended operating times. Such limitations highlight the pressing need for more reliable and precise control mechanisms.

Furthermore, conventional medical torquing devices often lack the adaptability and versatility necessary to meet the diverse needs of healthcare professionals. These devices are frequently designed for specific medical procedures, resulting in a fragmented landscape of tools that can be cumbersome for healthcare providers who require a single, versatile instrument capable of accommodating various instruments and procedures.

In addition to functional limitations, some existing devices suffer from ergonomic challenges, compromising the comfort and ease of use for healthcare professionals. Inefficiencies in torque transmission and control mechanisms can lead to operator fatigue, hindering the ability to maintain steady and precise instrument manipulation throughout the entirety of medical procedures.

As the field of medical torquing devices continues to evolve, addressing these longstanding issues with the prior art becomes increasingly imperative. Enhancing the overall functionality, precision, and user-friendliness of these devices is essential to meet the demands of modern medical practice, ultimately translating into improved patient outcomes and increased procedural efficiency. As a result, there exists a pressing need for improvements over the prior art and, more particularly, for the development of a medical torquing device that offers enhanced control, adaptability, and ergonomic design, addressing the shortcomings of existing solutions and ushering in a new era of medical instrument manipulation.

BRIEF SUMMARY OF THE INVENTION

A system and method for an advanced medical torquing device is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a medical device system is disclosed. The system comprises an outer body with a first u-channel extending longitudinally along its outer surface, a semi-tubular shaft that can transition between open and closed configurations, and an engaging element with locked and unlocked configurations. The engaging element is disposed in the first u-channel, allowing precise control of instrument rotation. The invention addresses limitations in existing medical torquing devices, providing enhanced precision, adaptability, and ergonomic design, thereby improving the efficiency and outcomes of minimally invasive medical procedures.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIG. 2 is an isometric view of the medical torquing device in an open configuration, according to an example embodiment;

FIG. 3 is an isometric view of the medical torquing device in a closed configuration, according to an example embodiment;

FIGS. 9A through 9E illustrate views of an inner body of the medical torquing device including a semi-tubular shaft and a handle having a second u-channel, according to an example embodiment;

FIGS. 11B through 11C illustrate exploded views of the medical torquing device illustrating the outer body and the inner body, namely the semi-tubular shaft, in the closed configuration, according to an example embodiment;

FIG. 11D is a detailed view projected down the longitudinal axis of the device illustrating the engaging element aligned with the open portion of the semi-tubular shaft in the closed configuration such that at least a portion of the engaging element may be disposed within the semi-tubular shaft in the locked configuration, according to an example embodiment; and FIG. 12 is a diagram illustrating the method of operating the medical torquing device, according to an example embodiment.

Figure 1:
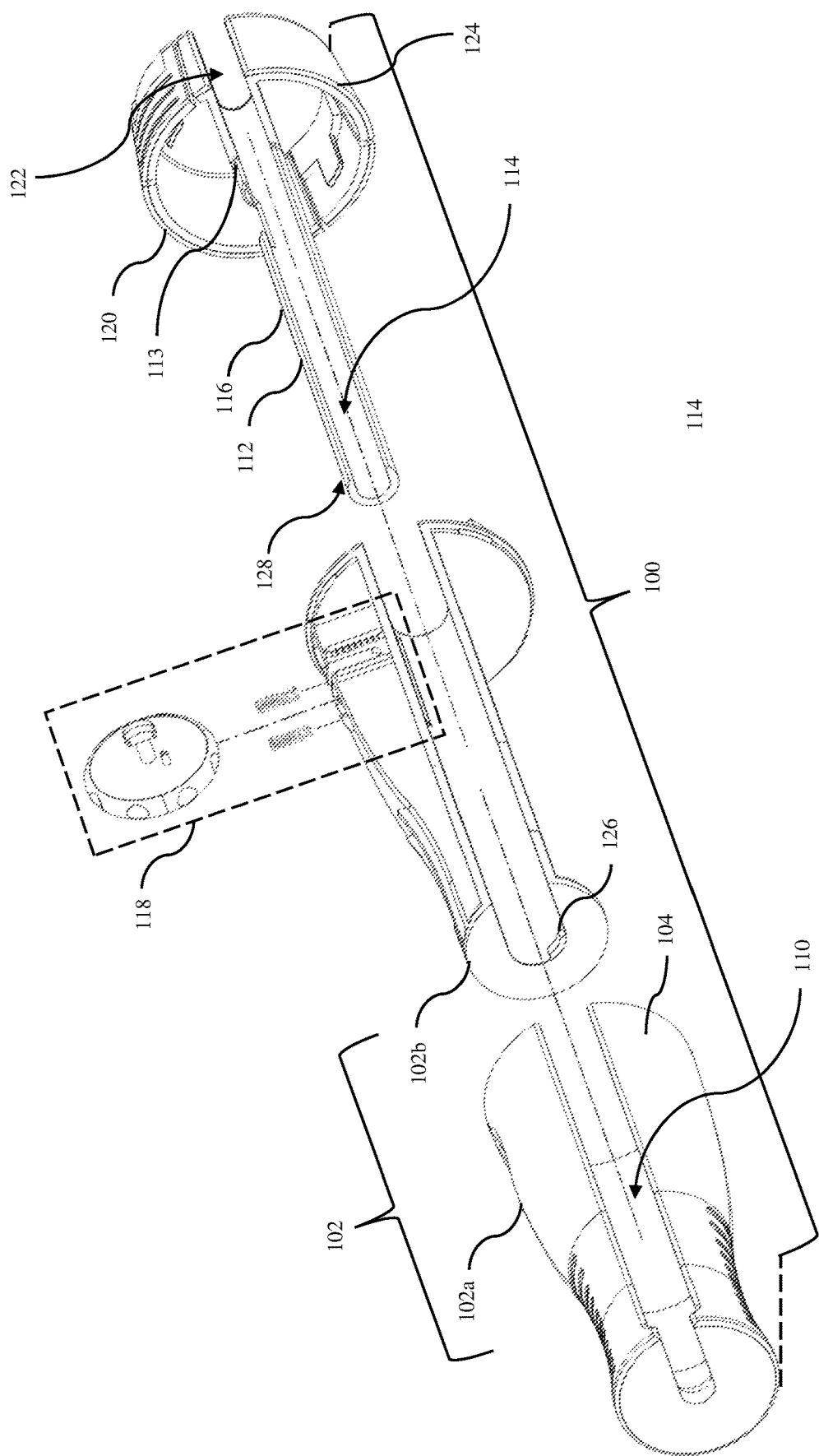
FIG. 1 is an isometric exploded view of a medical torquing device, according to an example embodiment.

The drawings accompanying this disclosure serve as illustrative examples of certain embodiments, demonstrating various aspects of the invention. It is important to note that these drawings, while providing valuable visual representation, are not exhaustive and do not limit the scope of the invention. Other embodiments that fall within the spirit and scope of the invention may be included, whether they are explicitly interpreted, perceived, or anticipated by the appended claims. The drawings are to scale, ensuring that the visual representation accurately reflects the proportions and relationships among components, further enhancing their utility in understanding the invention's design and functionality.

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a medical torquing device that mitigates the shortcomings commonly associated with conventional medical torquing devices. Specifically, the medical torquing device includes a combination of features to improve the usability, adaptability, and control of the device through various locking and securing mechanisms.

Specifically, the system includes an outer body with a first u-channel that accommodates multiple medical instruments by featuring an elongated slot contiguous to an inner portion. This adaptability to various medical instruments is a key feature of the system, addressing the need for versatility in medical procedures. The outer body is further detailed in FIGS. 8A through 8E.

Moreover, the inclusion of a handle with a second u-channel significantly enhances ease of operability, particularly in attaching the torquing device to multiple medical instruments. This design not only facilitates the precise rotation of the closed portion of the semi-tubular shaft and handle but also aligns it with and substantially covers the first u-channel. This strategic design feature effectively retains medical instruments, such as guidewires, within the inner portion of the u-channel, streamlining the attachment process and enhancing instrument control and manipulation.

The engaging element and/or torque-locking mechanism, comprising a slotted channel with teethed portions ensures secure instrument locking in the system's locked configuration. Conversely, in the unlocked configuration, it permits controlled movement of the instrument, addressing prior art limitations in terms of precision and stability.

Regarding the engaging element and/or torque-locking mechanism, which may include a double action wheel mechanism in certain embodiments, it ensures secure instrument locking in the system's locked configuration, thereby restricting rotational and longitudinal movement of the medical instrument when necessary for precise positioning and control. Conversely, in the unlocked configuration, it permits controlled movement of the instrument, allowing for both longitudinal and rotational adjustments. This addresses prior art limitations in terms of precision and stability.

The unique design of this medical torquing device allows for intuitive and efficient one-handed operation by the physician. With the handle's second u-channel, the physician can comfortably grasp and manipulate the device with a single hand, simplifying the attachment of the torquing device to various medical instruments. When it comes to controlling the instrument's movement, the physician can smoothly transition the torquing device between the unlocked and locked configurations with a simple hand movement. This operation not only permits controlled longitudinal and rotational adjustments of the medical instrument but also securely locks it in place when necessary for precise positioning. The torque-locking mechanism, featuring a slotted channel with teethed portions, ensures that these adjustments and securements are easily achieved with one hand, streamlining the procedure and enhancing the overall operability of the device.

Additionally, the semi-tubular shaft's opening and the detent-keyway arrangement represent pivotal components that significantly enhance the overall functionality, security, and structural integrity of the system. The presence of the semi-tubular shaft's opening, strategically positioned proximate to the slot in the outer body, plays a crucial role in the device's adaptability and precision. This opening facilitates the alignment of the closed portion of the semi-tubular shaft with the first u-channel, ensuring a secure and stable fit for medical instruments. Moreover, the detent-keyway arrangement, located within the inner portion of the first u-channel, serves as a multifunctional mechanism. Not only does it contribute to instrument stability, but it also plays a pivotal role in preventing unintended displacement of the semi-tubular shaft from the outer body. This dual functionality adds a critical layer of security, ensuring that the device maintains its structural integrity during rigorous medical procedures. Collectively, these design elements further enhance the system's functionality, security, and robustness, reaffirming its position as a pioneering solution in the field of medical torquing devices.

Furthermore, the system incorporates an ergonomic design that prioritizes user comfort and control. The device is characterized by its elongated shape, such that the term "elongated" signifies that it has an extended or stretched-out form, typically characterized by being longer than it is wide. Additionally, the profile of the outer body includes a sinuous shape that is characterized by a series of graceful, curving, or winding curves and bends, similar to the undulating pattern of a snake's movements. In this context, the outer body's sinuous shape means that it has a smoothly curved, meandering design along its length, rather than a straight or rigid form.

The device's elongated configuration is tailored for easy hand control, allowing physicians to manipulate it with precision. This elongated shape, particularly with a narrow distal portion, mimics the familiar grip of a writing instrument, providing an intuitive and natural feel during operation. To further enhance grip and ensure secure handling, the distal portion features a specially designed surface with enhanced texturing. This grip-enhanced surface promotes confident and stable control, reducing the risk of slippage or discomfort during extended medical procedures. The ergonomic considerations embedded within the system underscore its user-centric design, making it a valuable tool for healthcare professionals seeking both precision and comfort in their medical interventions.

In summary, the disclosed embodiments represent a significant advancement in the field of medical torquing devices, seamlessly integrating a range of innovative features to comprehensively address longstanding deficiencies in existing devices. These advancements center on precision, adaptability, and ergonomic design, collectively enhancing the overall functionality and usability of the system. Precision is a paramount consideration in medical procedures, and the system achieves this by enabling controlled movements and secure instrument locking, thereby improving the accuracy and predictability of medical interventions. Its adaptability to various medical instruments introduces a new level of versatility to the clinical setting, reducing the need for multiple specialized tools and streamlining procedures. Moreover, the system's ergonomic design, featuring an elongated, narrowed, grip-enhanced portion at the distal portion, offers both intuitive handling and operator comfort, reducing fatigue and promoting steady, confident control during critical phases of medical procedures. Collectively, these features redefine the landscape of medical torquing devices, promising enhanced precision, efficiency, and improved patient outcomes in minimally invasive medical procedures.

Referring now to the Figures, FIG. 1 depicts an isometric exploded view of a medical torquing device 100, according to an example embodiment. The medical torquing device 100 includes an outer body 102, comprising an outer surface 104, a proximal portion 106, and a distal portion 108. A first u-channel 110 extends longitudinally along the outer surface of the outer body from the proximal portion to the distal portion. A "channel" in the context of this invention refers to a groove or hollow structure within the device, typically shaped to accommodate and guide a specific component or instrument. In this case, the "first u-channel" specifically refers to the u-shaped channel designed to receive and secure medical instruments. Other channels with different shapes or functions may also be incorporated into the device's design to accommodate various needs or features consistent with the present disclosure.

The device also features a semi-tubular shaft 112, characterized by an open portion 114 and a closed portion 116, which is disposed within and rotatable within the first u-channel 110 of the outer body 102. A "semi-tubular shaft" refers to a structural component of the medical torquing device that is partially tubular in shape. It typically has an open portion and a closed portion. The semi-tubular shaft is designed to house and rotate around a medical instrument, such as a guidewire or catheter, within the first u-channel of the device's outer body. Its semi-tubular shape allows it to partially enclose the medical instrument, providing support and facilitating controlled rotation or movement of the instrument during medical procedures. The open portion of the semi-tubular shaft aligns with the first u-channel in the open configuration, allowing for the insertion and removal of the medical instrument, while the closed portion at least partially covers the first u-channel in the closed configuration, securing the instrument in place and preventing its movement.

The open portion of the semi-tubular shaft is characterized by a segmented arc opening. A segmented arc opening refers to a specific type of aperture or gap that appears in a curved or arched shape but is not continuous. Instead of forming a complete circle or curve, the semi-tubular shaft is divided into distinct segments, namely, the open portion and the closed portion. These segments may resemble individual sections or pieces within the overall curved shape. The term "segmented arc opening" is used to describe such a configuration where the curve or arc is not continuous but rather composed of separate, segmented portions. This opening defines the cross-sectional shape of the semi-tubular shaft in this region. The cross-section of the open portion is unique in that it is not fully enclosed; instead, it exhibits a distinctive C-shape. This C-shaped configuration allows the semi-tubular shaft to partially enclose the first u-channel while maintaining an open arc that provides access to the inner portion of the u-channel. When the device is configured in the open position, the C-shaped opening aligns seamlessly with the elongated slot 110a located in the first u-channel. This alignment streamlines the process of inserting or removing the medical instrument, such as a guidewire or catheter, through the u-channel. Similarly, rotating the device aligns the closed portion of the semi-tubular shaft with the slot 110a thereby securing the medical instrument within the inner portion of the channel.

The "semi-tubular shaft" features a cutout or opening 905 in its closed portion 116, shown in FIGS. 9A through 9C and in FIGS. 11A through 11D, where the opening 905 is positioned in close proximity to a portion of the engaging element 118. This opening is strategically located to be contiguous with the open portion of the semi-tubular shaft. When the device is in the open configuration, shown in FIGS. 11A and 11B, said opening allows the semi-tubular shaft to smoothly accommodate and fit around the portion of the engaging element that extends into the inner portion of the first u-channel. Without this opening, the engaging element could potentially encounter the edge of the semi-tubular shaft, hindering its rotation.

In the closed configuration, the closed portion 116 of the semi-tubular shaft covers at least a portion of the first u-channel 110. Conversely, in the open configuration, the open portion 114 of the semi-tubular shaft is at least partially aligned with the first u-channel 110. Additionally, the medical torquing device 100 incorporates an engaging element 118 capable of assuming both a locked configuration and an unlocked configuration, with at least a portion of the engaging element being disposed in the first u-channel 110 in the locked configuration.

When the semi-tubular shaft is in the closed position, as shown in FIGS. 11C and 11D, the engaging element can be translated or positioned within the inner portion of the first u-channel by passing through the open portion of the semi-tubular shaft. This configuration is also referred to as the locked position, and it ensures that the engaging element is securely located within the inner portion, thereby restricting the movement of the medical instrument. FIG. 11D serves to illustrate the closed position of the device. To transition between the closed and unlocked configuration (as depicted) and the closed and locked configuration, a specific movement of the engaging element 118, specifically the first wheel 1005, is required. This movement involves a translation in the directions denoted by arrow A, enabling a portion of the engaging element 505 to pass through the open portion 114 of the semi-tubular shaft. It should be noted that, during practical use, a medical device would typically be situated within the hollow or tubular channel of the semi-tubular shaft, adding to the functionality of the device.

Moreso, the medical torquing device features a handle 120 that is securely attached to an end portion 113 of the semi-tubular shaft and which such handle includes a second u-channel 122 and a closed portion 124. Similar to the first channel, the second channel, refers to a groove or hollow structure within the device, typically shaped to accommodate and guide a specific component or instrument. In this case, the "second u-channel" specifically refers to the u-shaped channel designed to receive and secure medical instruments. Other channels with different shapes or functions may also be incorporated into the device's design to accommodate various needs or features within the spirit and scope of the present disclosure. In a corresponding manner, the second u-channel may also incorporate a slot 910 and an inner portion 915, shown in FIGS. 9D and 9E, analogous to those found in the first u-channel. The inner portion 915 is contiguous to the inner portion or hollow portion of the semi-tubular shaft, which forms a portion of the inner portion fo the first u-channel. This second u-channel's design aligns with that of the first u-channel, ensuring consistent functionality throughout the device. Specifically, the slot 910 in the second u-channel runs is contiguous to the inner portion 915, each of which run parallel to the slot 110a and inner portion 110b of the outer body, mirroring the configuration of the first u-channel. This parallel design maintains uniformity in the device's operation, allowing for seamless use and compatibility with medical instruments in both u-channels.

In the context of the medical torquing device, the term "handle" refers to a component that is designed for grasping or manipulation by an operator. The handle may function as a knob, and when rotated, it transforms the device into the closed position, effectively retaining the medical instrument within the inner channel. This handle/knob provides a means for the operator to control the device's configuration and securely lock it when needed during medical procedures. In other example embodiments, the handle may also be considered as an engaging element. This dual functionality allows for a streamlined design where the handle serves the purpose of both manipulating the device and engaging it to lock or unlock, providing added convenience and simplicity in operation.

The handle of the medical torquing device may incorporate a guide or stop element 920, shown in FIG. 9A. This guide or stop serves a dual purpose within the device. Firstly, it acts as a rotational guide, ensuring that the handle rotates precisely and smoothly in conjunction with the outer body. This precise rotation is crucial for controlling the device's configuration, particularly when transitioning between the open and closed positions. Additionally, the guide or stop may also function as a connection point between the handle and the outer body. This connection enhances the structural integrity of the device, ensuring that the handle remains securely attached to the outer body during operation. Moreover, the guide or stop can serve as a mechanism to limit the degrees of rotation, preventing over-rotation and providing tactile feedback to the operator when the device is in the desired configuration. This feature adds an additional layer of control and safety to the device's operation. The handle is equipped with a grip 925, which not only aids in the ease of rotating the handle but also serves as a visual indicator for aligning the first channel and the second channel. Additionally, they may be squeezed and twisted in a specific manner, providing a mechanism for disassembling the inner body from the outer body.

Furthermore, the inner portion 110b of the first u-channel may include a detent 126. A detent is a mechanical component or feature commonly used in various devices and mechanisms to provide a secure, stable, and often indexed position. It typically consists of a recessed or protruding element, often with a specific shape or design, that interacts with corresponding components to create resistance or a locking mechanism. Detents are often used to prevent unintentional movement, maintain alignment, or facilitate controlled positioning in mechanical systems. In the context of the medical torquing device, the detent within the inner portion of the first u-channel serves as a locking point, ensuring that the semi-tubular shaft can securely engage and remain in place when needed during medical procedures and while transitioning between the open and closed configurations. Simultaneously, the semi-tubular shaft of the medical torquing device is equipped with a keyway 128. A keyway is a specific type of slot or groove that is typically designed to accommodate a key or a similar device for the purpose of guiding, securing, or aligning components within a mechanical system. It often has a unique shape or configuration that corresponds to the shape of the key, ensuring that the key can fit into the keyway in only one specific orientation. Keyways are commonly used in various applications, including machinery, locks, and precision instruments, to control movement, prevent rotation or displacement, and maintain proper alignment. In the context of the medical torquing device, the keyway on the semi-tubular shaft is engineered to operatively engage with the detent within the first u-channel, securely locking the shaft in place and allowing for controlled and precise manipulation of medical instruments during procedures.

The detent, positioned within the inner portion of the first u-channel, serves as a secure locking mechanism. It provides a defined and stable point of engagement for the semi-tubular shaft. In turn, the semi-tubular shaft is configured with a keyway designed to operatively engage with the detent. When the keyway aligns with the detent, it securely locks the shaft in place, preventing unintended movement or rotation.

Referring to FIGS. 1 through 3, the outer body 102, a pivotal component of the disclosed medical torquing device, is a tubular structure with an elongated shape, extending from its proximal portion 106 to its distal portion 108. It serves as the primary housing and framework for the device, encompassing essential internal components. As depicted in FIG. 1, the outer body 102 comprises two integral components: a shell or housing 102a, and an inner structure 102b. In a broad sense, the outer body 102 encompasses the entirety of these components, serving as the primary framework and housing for the internal mechanisms of the medical torquing device. It is important to note that in certain embodiments, the shell and inner structure 102b may form a unified or uniform body, streamlining the device's design and ensuring seamless integration of both structural and functional elements. The outer body 102 is characterized by a smooth and durable outer surface 104, designed for ease of handling and sterilization in clinical settings.

The outer body of the medical torquing device exhibits a distinctive serpentine curvature, characterized by its gently curving shape that imparts ergonomic advantages during use. Notably, as it approaches the distal portion of the device, the outer body features a narrowing portion 103. This deliberate design choice emulates the ergonomic profile of a writing instrument, enhancing operator comfort and precision during medical procedures. The narrowing portion 103 encourages a secure and natural grip, akin to holding a pen or pencil, which is particularly advantageous for one-handed operation and delicate maneuvers.

The outer body may be constructed from a range of biocompatible materials, including but not limited to, stainless steel, known for its exceptional durability and resistance to corrosion; titanium, a lightweight and strong material often used in medical implants; medical-grade plastics such as polyethylene and polycarbonate, offering versatility and ease of sterilization; aluminum, valued for its strength-to-weight ratio; ceramic, known for its resistance to wear and high-temperature stability; silicone, chosen for its flexibility and softness; biodegradable polymers like polylactic acid, suitable for temporary medical applications; carbon fiber, offering a combination of strength and lightness; PEEK (Polyetheretherketone), prized for its chemical resistance; and nickel-titanium (Nitinol), known for its shape memory properties. This diverse selection of materials allows for tailored design considerations, ensuring the outer body's biocompatibility, durability, and suitability for specific medical applications.

To further optimize grip and control, the narrowing portion 103 is equipped with a grip-enhanced texture 105. This texture comprises strategically placed patterns or surface features that promote a secure grasp, minimizing the risk of slippage during critical phases of medical procedures. In one embodiment, the grip-enhanced texture 105 on the outer body may incorporate strategically positioned protrusions on the outer surface. These protrusions are designed to provide an enhanced grip for the operator, minimizing the risk of slippage during critical medical procedures. Materials suitable for creating the grip-enhanced texture 105 encompass a range of options, including silicone, known for its flexibility and tactile properties; rubber, which provides a soft yet grippy surface; thermoplastic elastomers (TPE), combining the characteristics of rubber and plastic for enhanced grip; textured plastics that can be molded with textured patterns; and non-slip coatings, specialized applications with grip-enhancing properties. The choice of material for the grip-enhanced texture 105 can be tailored to meet specific ergonomic and usability requirements, ensuring that the operator can maintain precise control of the medical torquing device under various conditions.

The combination of the serpentine curvature and the grip-enhanced texture not only enhances operator comfort but also contributes to the overall usability and efficiency of the medical torquing device, aligning it with the familiar ergonomics of a writing instrument for intuitive and precise instrument manipulation.

FIG. 2 provides a visual representation of the medical torquing device in the open configuration 200. In this state, the device is prepared to receive a medical instrument within the first u-channel 110. The open configuration allows for seamless insertion and positioning of the medical instrument within the device. This is a critical step in preparing the device for medical procedures, ensuring that the instrument can be easily introduced into the inner portion of the u-channel. Running longitudinally along the outer surface of the outer body 102 is a first u-channel 110, which provides a crucial pathway for the insertion and manipulation of medical instruments. The medical torquing device is a versatile tool designed to accommodate a wide range of medical instruments, ensuring precise and controlled manipulation during procedures. These medical instruments may include, but are not limited to, guidewires, catheters, endoscopes, surgical instruments, orthopedic instruments, dental instruments, neurological instruments, cardiac instruments, gastrointestinal instruments, and urological instruments, among others. The device's adaptability to various instruments reflects its utility across different medical specialties and procedures, where torque control plays a critical role in achieving safe and accurate outcomes.

Figure 8A:
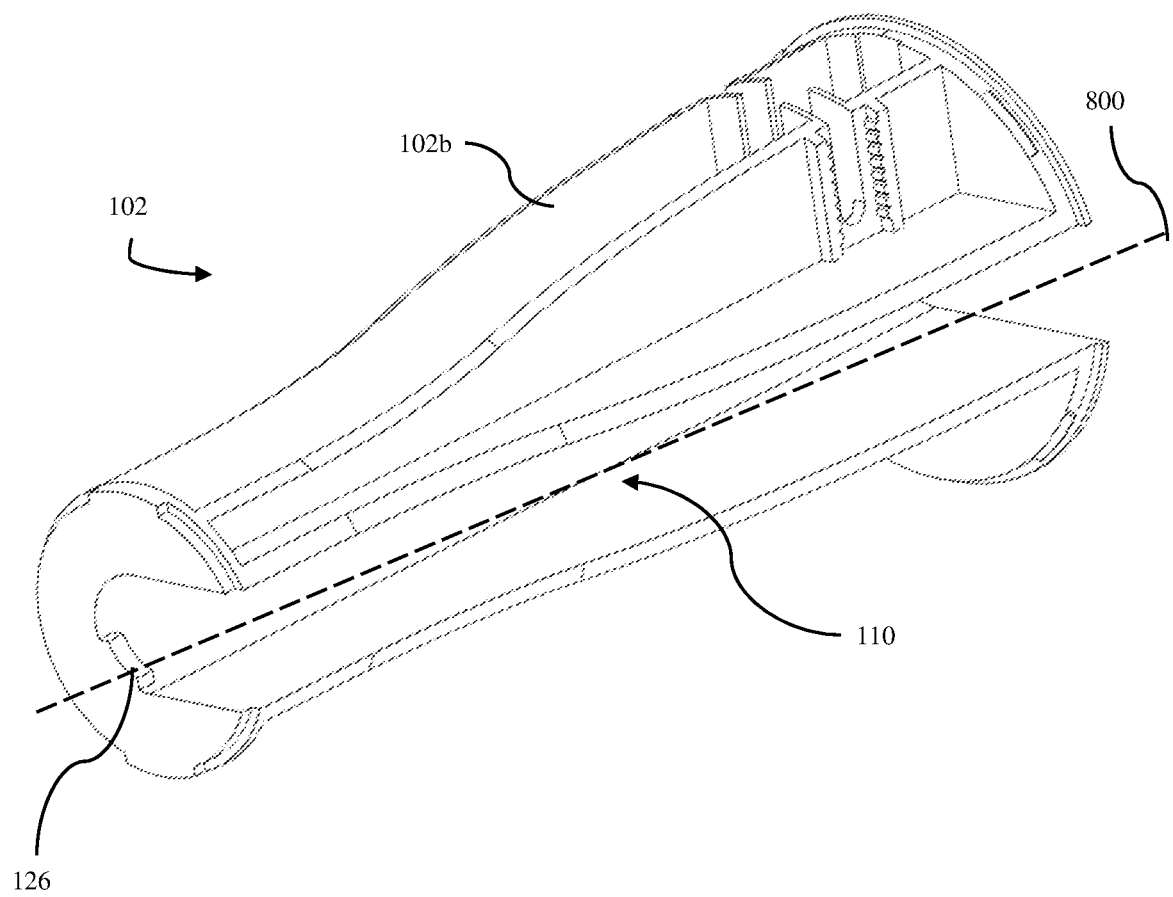
FIGS. 8A through 8E illustrate views of an outer body of the medical torquing device, according to an example embodiment.
Figure 8B:
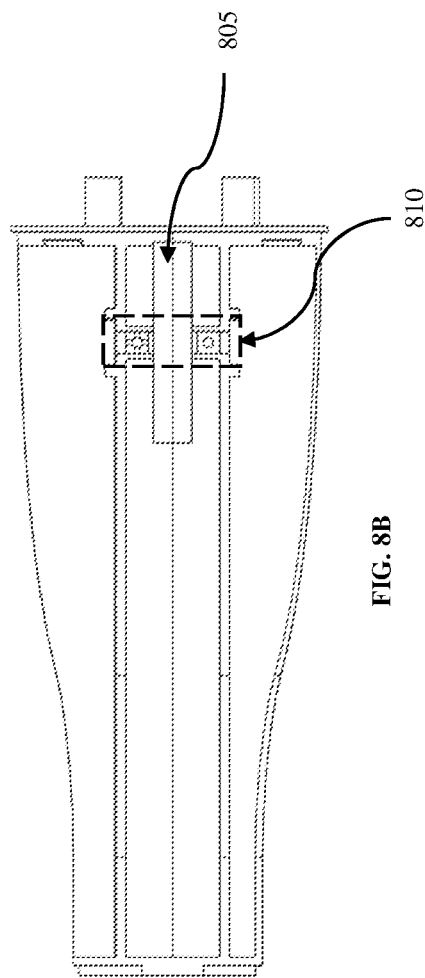
Figure 8E:
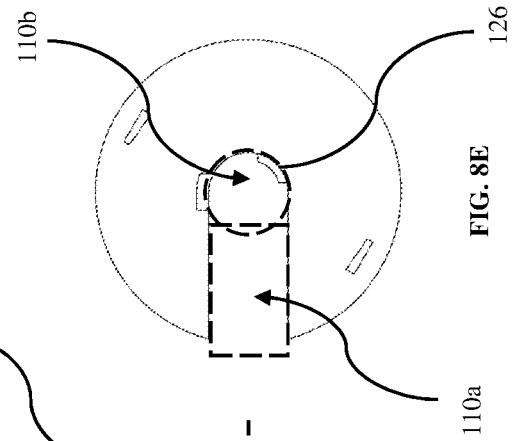
Figure 8D:
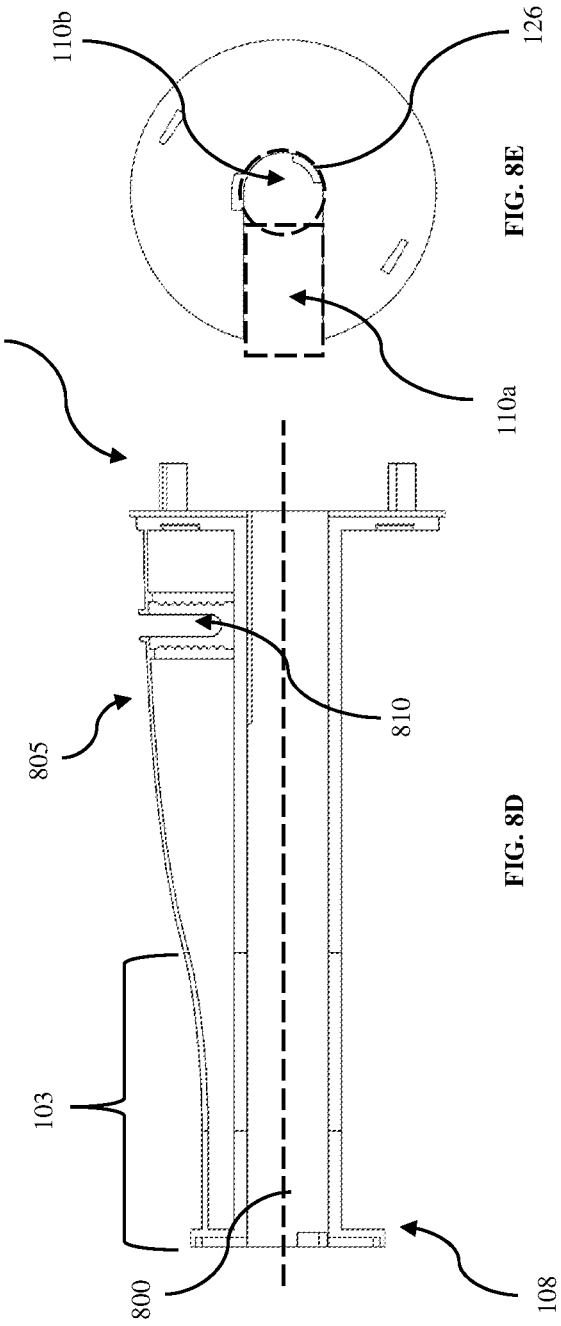
Figure 8C:
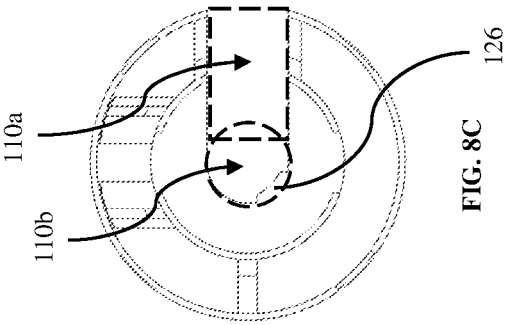

The medical torquing device further includes a first u-channel 110, which longitudinally extends about the longitudinal axis 800, shown in FIG. 8D, of the device, and is a channel-shaped feature along the outer surface of the outer body 102 of the medical torquing device. It serves as a precise pathway for the insertion and manipulation of medical instruments. The first u-channel is designed to securely hold and guide these instruments during medical procedures, ensuring controlled and accurate movements within the patient's body. It is a fundamental component of the device's functionality, facilitating the operator's ability to navigate and manipulate medical instruments with precision and ease.

The first u-channel 110 may be defined by an elongated slot 110a that is contiguous to an inner portion 110b. An elongated slot of the channel refers to a narrow, extended opening or groove that runs along the length of the channel 110 within the medical device. This slot is characterized by its elongated shape, which means it is longer in one dimension compared to its width, making it suitable for accommodating various components or objects that need to move or be positioned within the channel. The term "elongated slot" is used to emphasize the elongated or extended nature of this opening, which is typically designed to facilitate the movement or placement of elements within the channel. When the slot is described as "contiguous to the inner portion" within the context of the first u-channel, it means that the elongated slot and the inner portion are physically connected or adjacent to each other without any gaps or interruptions. In other words, there is a seamless and continuous transition between the slot and the inner portion. The elongated slot 110a is a linear opening or groove running along the length of the first u-channel, adjacent to its inner portion 110b. Importantly, the semi-tubular shaft of the medical torquing device is intentionally situated within this inner portion 110b.

Conversely, FIG. 3 illustrates the medical torquing device in the closed configuration 300. In this state, at least a portion of the inner portion of the first u-channel 110 is enclosed or partially covered, preventing the seamless insertion or removal of the medical instrument. This retains the medical instrument securely within the inner portion of the u-channel during procedures. The inner portion, defined by a channel extending through the device, is ideally cylindrical, featuring a circular and/or elliptical cross-section. However, it's important to note that the functionality of the device is not limited to these particular shapes, ensuring versatility in accommodating various medical instruments and their specific requirements.

Figure 4A:
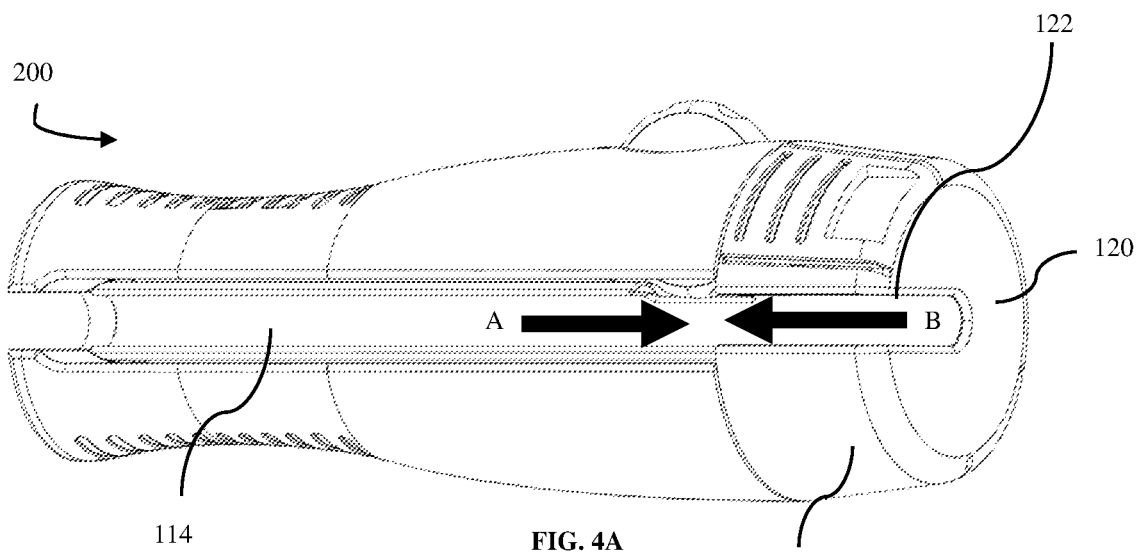
FIGS. 4A through 4C illustrate side perspective views of the medical torquing device in transitionary states between the open configuration and the closed configuration, according to an example embodiment.
Figure 4B:
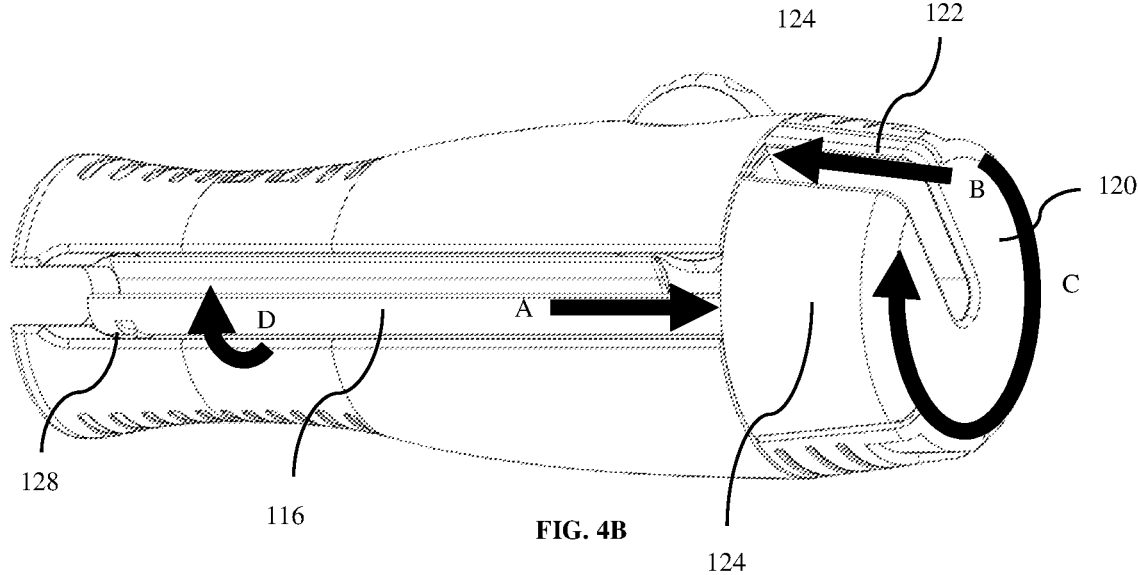
Figure 4C:
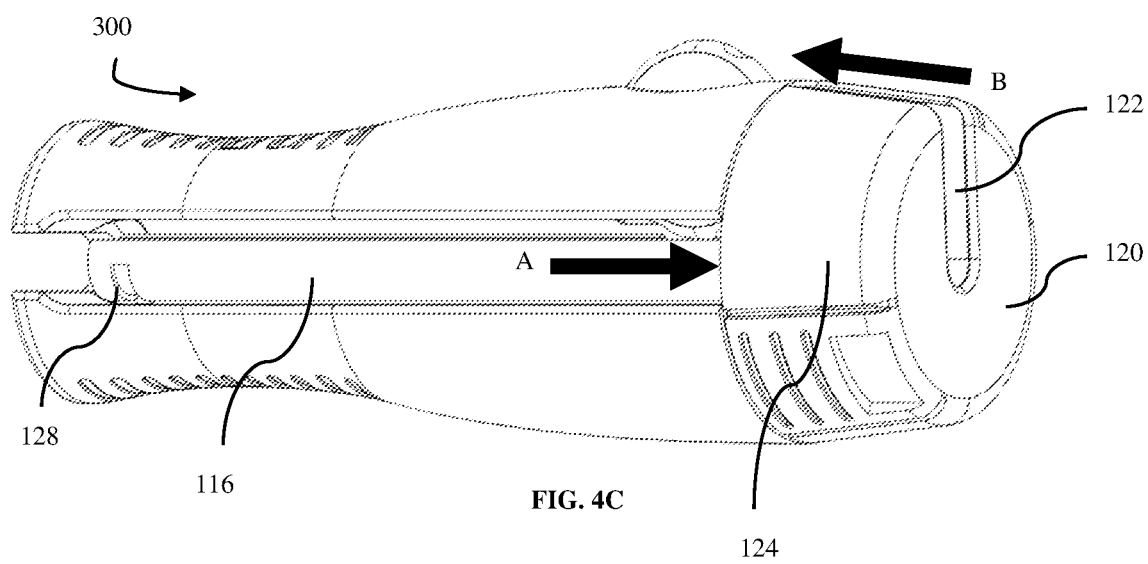

Referring now to FIGS. 4A through 4C, these illustrative figures provide a detailed depiction of the medical torquing device's transition between the open configuration and the closed configuration. This transitional process is a critical aspect of the device's functionality, showcasing how it accommodates the receipt and secure retention of a medical instrument. Referring to FIG. 4A, in this initial state, the device is positioned in the open configuration 200, as also demonstrated in FIG. 2. The first u-channel and the second u-channel within the handle are aligned, permitting the device to receive a medical instrument with ease. As shown in FIGS. 4A through 4C, arrows A and B are positioned in proximity to the longitudinal axis of the first u-channel and the second u-channel, respectively. These arrows are representations to indicate the alignment or misalignment between the two channels within the medical torquing device for illustrative purposes. They do not denote any particular direction or applied force during device operation.

In FIG. 4A, the alignment of the first u-channel and the second u-channel is clearly illustrated along their respective longitudinal axes. Arrow A, indicative of the first u-channel, aligns with Arrow B, representing the second u-channel, along the longitudinal axis. This alignment allows for the easy insertion and positioning of a medical instrument within the medical torquing device, facilitating efficient and precise medical procedures.

As the device begins its transition towards the closed configuration, as shown in FIG. 4B, the alignment between the first u-channel and the second u-channel gradually shifts. This alignment change is achieved through the rotation of the handle in the direction denoted by arrow C, and the corresponding rotation of the semi-tubular shaft in the direction denoted by arrow D, each of which is guided by the device's design and mechanics. In this stage, the handle and the semi-tubular shaft are in the process of rotating, guided by the keyway on the shaft engaging with the detent within the first u-channel's inner portion. This guided rotation is a critical aspect of the device's operation, ensuring controlled movement and precise alignment.

As the rotation continues, the closed portion of the semi-tubular shaft, represented by the closed portion 116, is brought into position to at least partially enclose the inner portion of the first u-channel. The closed portion effectively encloses or partially encloses the inner portion, thereby disrupting the contiguous access within the first u-channel, namely, between the elongated slot and the inner portion. This enclosure ensures that nothing can pass through the elongated slot and into the inner portion from the outside, and conversely, anything within the inner portion cannot exit through the elongated slot.

Simultaneously, as the alignment between the first u-channel and the second u-channel in the handle becomes misaligned, the closed portion of the handle 124 also serves to at least partially enclose the inner portion. This enclosure ensures that nothing can pass through the elongated slot and into the inner portion from the outside, and conversely, anything within the inner portion cannot exit through the elongated slot. This closing mechanism securely retains the medical instrument within the inner portion.

Finally, in FIG. 4C, the medical torquing device has reached the closed configuration 300. Here, the alignment between the u-channels is obstructed by the closed portion of the handle and the inner portion of the u-channel is isolated from the elongated slot of the u-channel. Notably, the first u-channel and second u-channel are intentionally misaligned along their respective longitudinal axes. Arrow A, representing the first u-channel, and Arrow B, representing the second u-channel, no longer align as they did in the open configuration (FIG. 4A). This deliberate misalignment enables the locking and secure retention of a medical instrument within the inner portion of the u-channel. The transition illustrated in these figures exemplifies the device's seamless adaptability, allowing healthcare professionals to operate with precision and confidence. The medical torquing device can seamlessly transition from the closed configuration (as shown in FIG. 4C) to the open configuration (as depicted in FIG. 4A) by simply reversing the rotation of the handle in the opposite direction of the rotational indicators represented by arrows C and D in FIG. 4B. This reversal of rotation re-aligns the first u-channel and the second u-channel, facilitating the removal of a medical instrument.

Figure 5C:
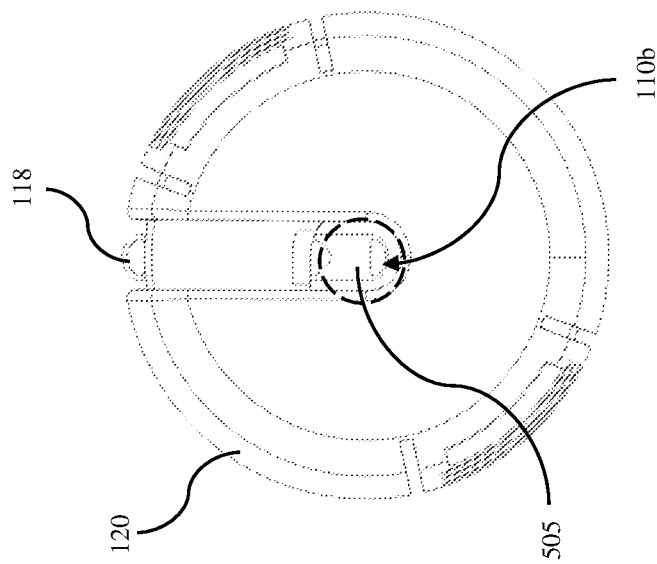
FIGS. 5A through 5C illustrate proximal side views of the medical torquing device in transitionary states between the open and unlocked configuration and the closed and locked configuration, according to an example embodiment.
Figure 5B:
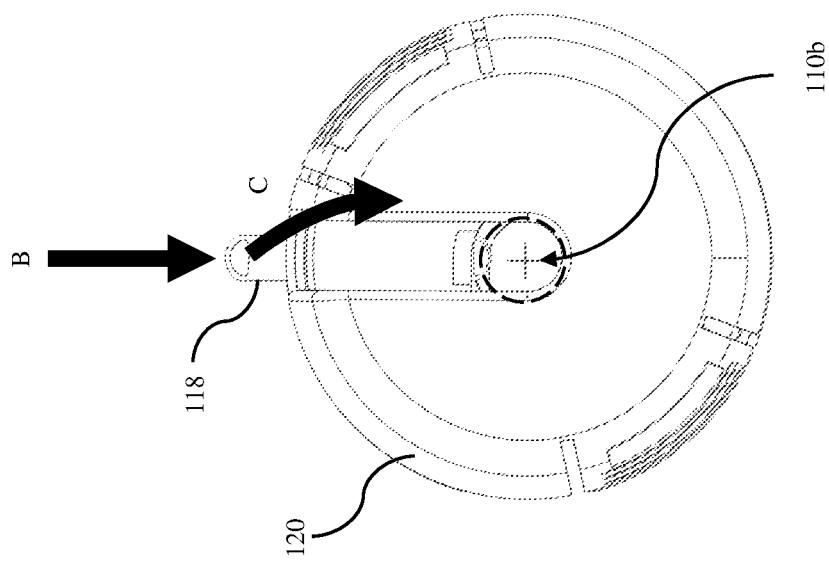
Figure 5A:
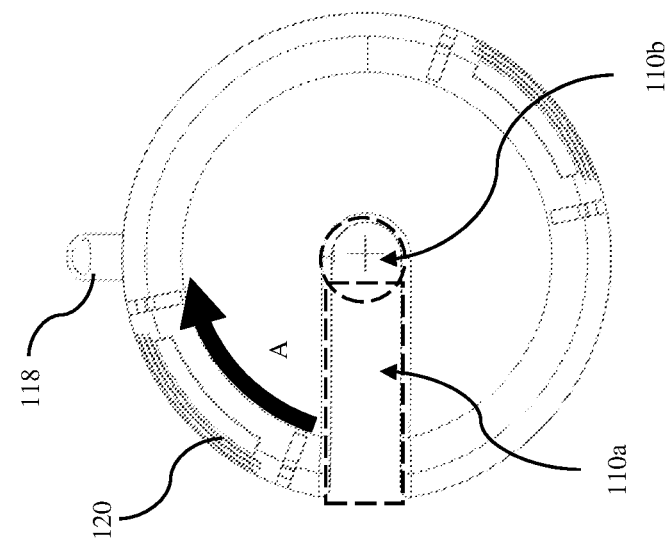

Referring now to FIGS. 5A through 5C, these provide a detailed perspective from the proximal side, projecting down the longitudinal axis of the medical torquing device. In FIGS. 5A through 5C, the longitudinal axis of the device is clearly indicated by a cross, concentrically marked about the device. This visual reference serves as a helpful guide for viewers, highlighting the orientation and alignment of the device's key components and the direction of movement during the engagement and locking process. The longitudinal axis demarcation aids in understanding the precise interactions and adjustments made by the operator while operating the medical torquing device, enhancing the clarity of the device's functionality as depicted in these illustrations.

FIGS. 5A through 5C depict the intricate interactions between the handle, engaging element, and the inner portion of the first u-channel as the device transitions from the open and unlocked configuration to the closed and locked configuration. In FIG. 5A, in this initial stage, the device is in the open and unlocked configuration, which is similarly depicted in FIG. 2. The operator initiates the rotation of the handle in the direction denoted by arrow A, which in turn rotates the semi-tubular shaft guided by the keyway and detent mechanism, to transition into the closed configuration. The closed configuration is shown in FIG. 5B. As the handle continues its rotation, the inner portion 110b of the first u-channel is effectively closed off from the slot 110a, thereby securing a medical instrument within. It is important to note that while the medical instrument is not explicitly shown within the inner portion, it is understood that the inner portion serves as a channel extending through the longitudinal axis of the device. Therefore, the medical instrument would indeed be disposed within this channel, and the torquing device would be securely positioned around a portion of the medical instrument.

In the closed configuration, the design of the medical torquing device offers a remarkable advantage to the operator. The operator possesses the capability to seamlessly feed the medical instrument through the torquing device, allowing the instrument to further penetrate into the patient's body. Within the confines of the inner portion, the medical instrument experiences a unique freedom—it can freely translate longitudinally and rotate with ease. This exceptional combination of secure retention and uninhibited movement is a defining feature of the device's design, granting healthcare professionals the confidence and precision required for successful medical interventions. With the device securely in place, the operator can navigate the medical instrument within the patient's body, knowing that it remains firmly held while offering the necessary flexibility for the procedure at hand.

As the operator skillfully guides and adjusts the medical instrument with one hand, the torquing device becomes a natural extension of their capabilities. Held securely in the operator's other hand, the torquing device serves as a versatile tool. Through the manipulation of the engaging element, the operator can effortlessly control and fine-tune the movement of the torquing device. This dynamic coordination allows for the precise restriction or enhancement of the torquing device's movements, ensuring that it responds seamlessly to the operator's intentions. This single-handed control mechanism simplifies the procedure and enhances the operator's dexterity, contributing to the overall efficiency and success of medical interventions.

To transition the medical torquing device into its locked configuration, the operator initiates a critical step by engaging the device's central component, the engaging element. This pivotal action is visually depicted in FIG. 5B, where arrows indicate the direction of the forces via the operator's engagement with the engaging element. An engaging element is a component or mechanism within a system or device that is designed to interact with other elements or parts to achieve specific functions. Engaging elements typically involve a physical engagement or interaction that results in the activation or operation of certain features or functions within the system. The design and purpose of engaging elements can vary widely depending on the context and application, but their fundamental role is to facilitate controlled interactions and movements within the system, often serving as a means to secure, lock, or manipulate components as needed. Engaging elements are commonly found in various mechanical and electronic systems, contributing to their functionality and efficiency.

In one embodiment, the engaging element is a double-action engaging element. A double-action engaging element typically refers to a mechanism that can perform two distinct actions or functions within a device. In the context of the medical torquing device, it suggests that the engaging element can execute two specific actions or movements, possibly in opposite directions, to achieve certain functionalities. This design allows for increased control, precision, and flexibility in manipulating the device and securing medical instruments.

As depicted in FIG. 5B, the engaging element within the medical torquing device represents a double-action engaging element. The configuration of a double-action engaging element requires the operator to perform two distinct actions simultaneously for precise instrument locking. To initiate the engagement process, the operator applies a downward force on the engaging element in the direction denoted by arrow B, causing at least a portion 505 of the engaging element to enter the inner portion of the u-channel. This downward movement of the engaging element serves to impede the movement of the medical instrument, ensuring its secure retention. The application of a downward force on the engaging element provides for a momentary locking position that restricts the movement of the medical instrument. Simultaneously, or as per the operator's discretion, the operator may also execute a rotation or sliding action of the engaging element, effectively locking it in place within the device to maintain the downward force on the medical instrument. The rotation or sliding of the engaging element, which is a rotation of a wheel in FIG. 5B, is shown by the direction denoted by arrow C. This dual-action engagement mechanism exemplifies the device's commitment to providing healthcare professionals with unparalleled control and precision during medical procedures, enhancing both the device's functionality and operator's experience.

The engaging element, further defined herein according to the example embodiments of FIGS. 6A through 7C and FIGS. 10A through 10C, offers the operator a remarkable degree of control during medical procedures. Its wheel-like design allows for precise adjustment of both the downward pressure on the medical instrument and the locking mechanism. This dual functionality enables the operator to smoothly transition between the locked and unlocked configurations as needed throughout the procedure. It's important to note that the operator has the flexibility to apply only a downward force on the engaging element, restricting the movement of the medical instrument without necessarily configuring the device into a permanent or temporary locked position. This adaptability underscores the device's versatility and responsiveness to the operator's requirements, making it a valuable tool in medical interventions that demand precision and control. FIG. 5C illustrates the medical torquing device in its closed and locked configuration, with a portion of the engaging element intentionally disposed within the inner portion of the u-channel.

Referring now to FIGS. 6A through 10C, the engaging element within the medical torquing device takes center stage in these illustrations. These figures provide a comprehensive view of the engaging element's behavior, movement, and interaction with other components of the device. This detailed visual representation offers valuable insights into how the engaging element operates, engages with the u-channel, and contributes to the locking mechanism. These figures play a pivotal role in elucidating the intricacies of the device's functionality, enhancing the understanding of its operation during medical procedures.

In one example embodiment, the engaging element within the medical torquing device is a multifaceted component, expertly designed to ensure precise and secure operation. The engaging element is comprised of several integral elements, each playing a crucial role in its function. The engaging element may include a slot 805, shown in in FIG. 8B illustrating a top view of the outer body, thoughtfully integrated along the outer surface of the outer body, providing convenient access to the device's inner workings. Within this slot, a slotted channel 810, shown in in FIG. 8B, takes form. The slot 805, in the context of the medical device, is an aperture or opening that is deliberately designed within the outer body of the device. Its primary function is to serve as a receptacle for a portion of the engaging element, thereby allowing the engaging element to interact with the inner portion of the channel and/or the inner body of the device. Furthermore, the slot 805 also functions as a passageway, providing access to the inner portion of the channel and potentially the inner body, depending on the device's configuration. This access is crucial for the engagement and operation of the engaging element within the channel, contributing to the device's overall functionality.

Figure 7A:
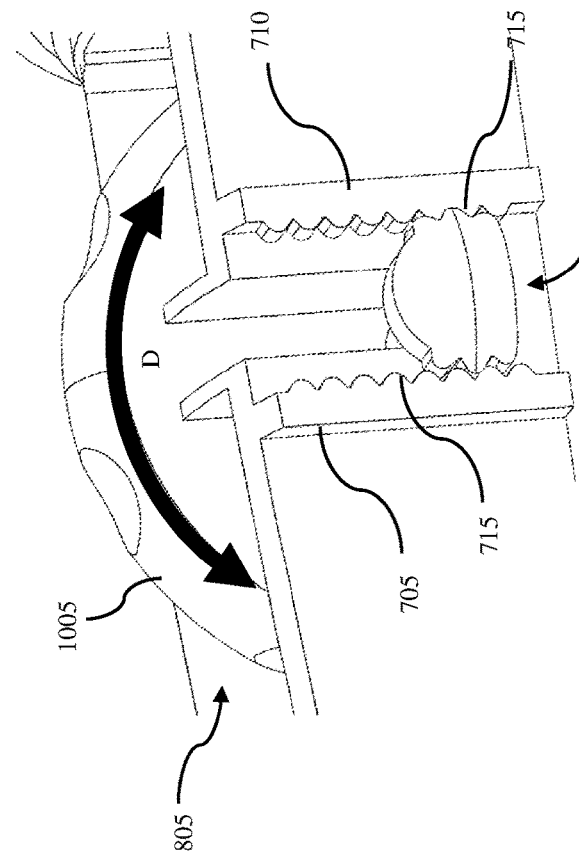
FIGS. 7A through 7C illustrate detailed views of an engaging element of the medical torquing device in transitionary states between the unlocked configuration and the locked configuration, according to an example embodiment.
Figure 7B:
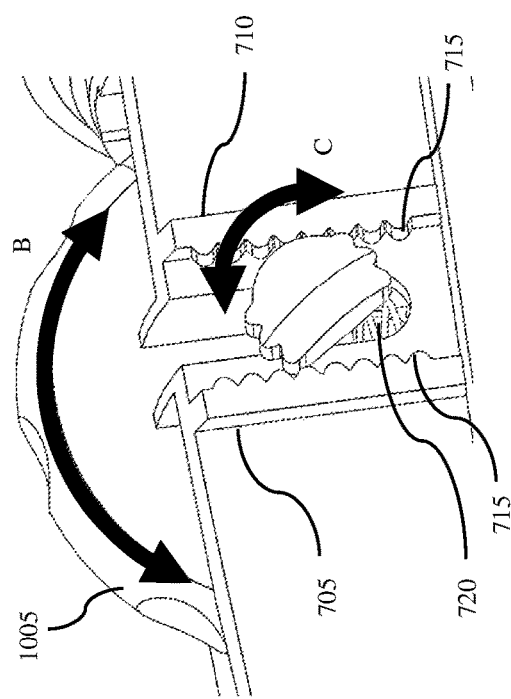
Figure 7C:
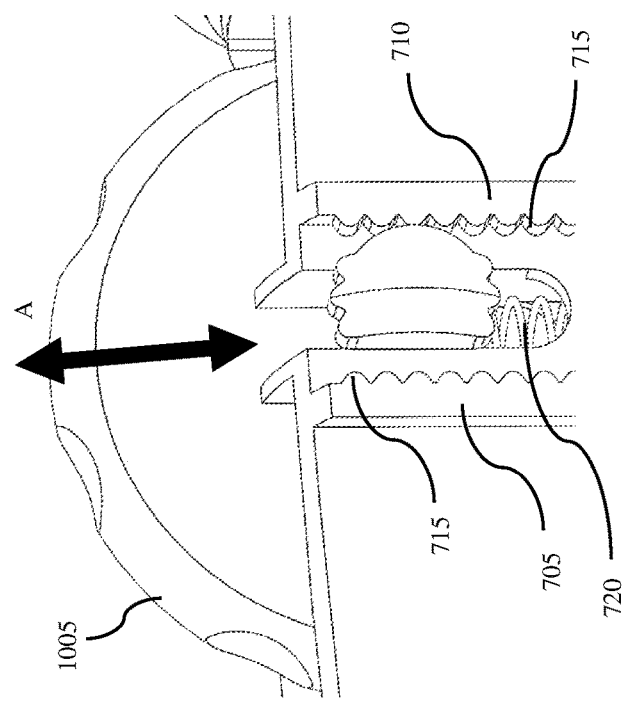

The slotted channel includes a first channel wall 705, shown in FIGS. 7A through 7C, opposing a second channel wall 710, shown in FIGS. 7A through 7C. In this context, the term "slotted channel" refers to a channel or passage that contains slots or openings. These slots or openings within the channel may intersect with or connect to another specific slot or passageway, such as passageway or slot 805. This intersection or connection between the slotted channel and slot/passageway 805 may be relevant for the device's functionality, allowing components to move, engage, or interact as needed within the system.

The plurality of teeth 715, shown in FIGS. 7A through 7C, disposed on the channel walls of the slotted channel within the engaging element are integral components designed for precise control and secure engagement. These teeth are arranged along both the first channel wall and the second channel wall, forming a set of interlocking elements that interact with other components of the device. These teeth are characterized by their small, uniformly spaced projections or ridges that extend inward from the channel walls. The design of these teeth is carefully engineered to ensure a reliable and consistent grip when the engaging element is in its locked configuration. When engaged, these teeth interact with corresponding features within the device, such as the teethed portion of the second wheel, creating a secure and stable connection.

The teeth featured on the channel walls of the slotted channel within the engaging element are intentionally designed with rounded profiles. This design choice serves to enhance the overall functionality and user experience of the medical torquing device. The rounded shape of these teeth contributes to smooth and seamless movements during the transition between the locked and unlocked configurations. The rounded edges of these teeth minimize friction and resistance, allowing for effortless rotation and sliding of the engaging element within the slotted channel. This design consideration is particularly crucial during medical procedures, where precision and ease of use are paramount. The smooth, rounded teeth facilitate controlled adjustments and ensure that the device can be securely locked or unlocked with minimal effort. By reducing the risk of snagging or jamming, the rounded teeth enhance the reliability and predictability of the device's operation. This design feature aligns with the device's ergonomic and user-friendly characteristics, providing healthcare professionals with a tool that offers both precision and ease of use, ultimately improving the quality of patient care.

Figures 10A, 10B, 10C:
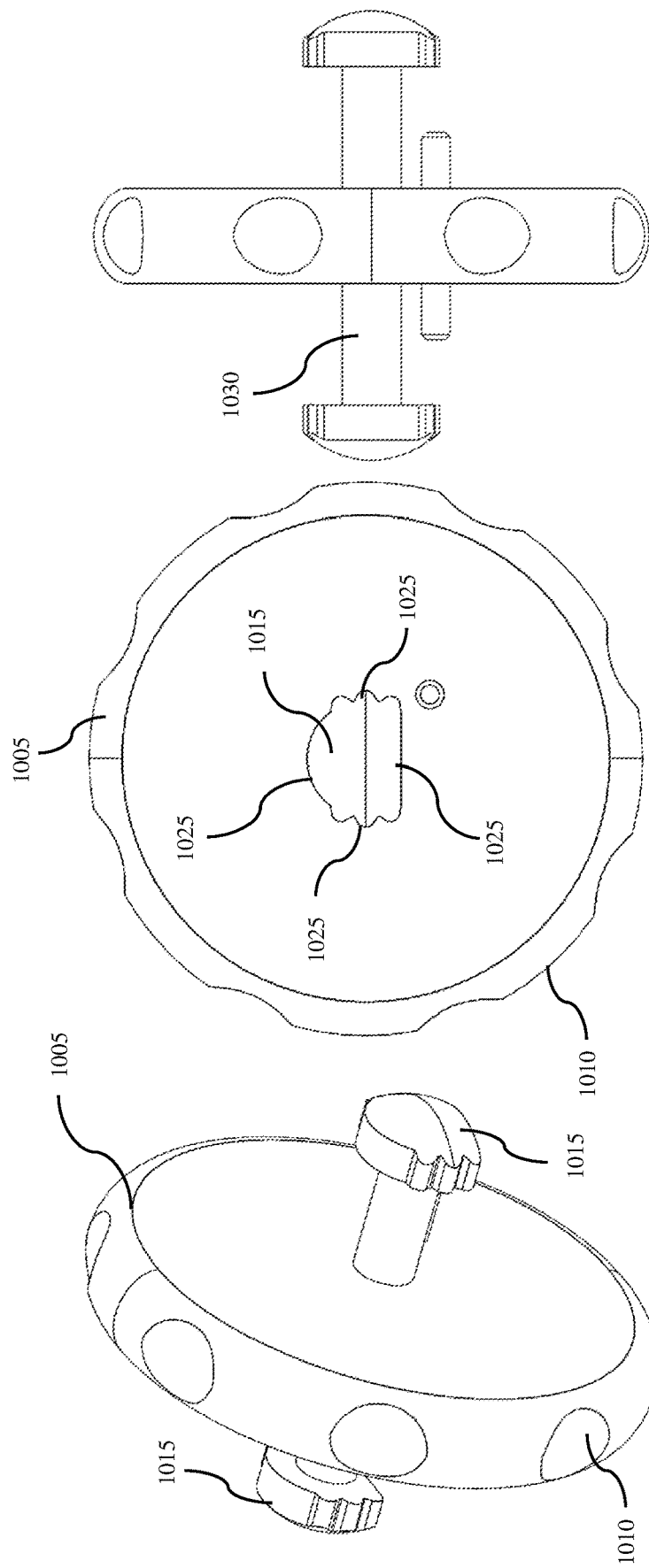
FIGS. 10A through 10C illustrate views of a component of the engaging element of the medical torquing device, according to an example embodiment.
Figure 11A:
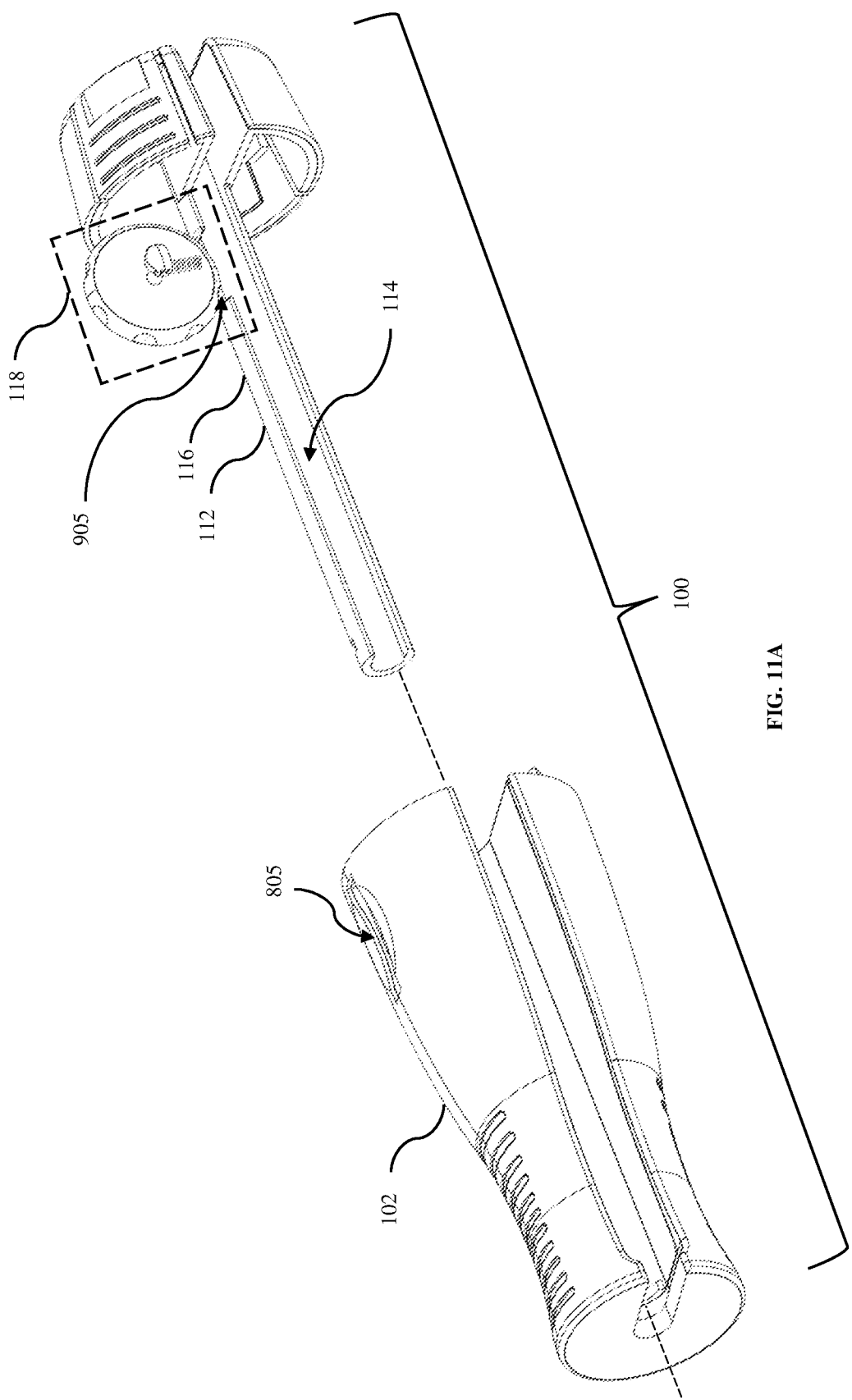
FIG. 11A is an exploded view of the medical torquing device illustrating the outer body and the inner body, namely the semi-tubular shaft, in the open configuration, according to an example embodiment.
Figure 11B:
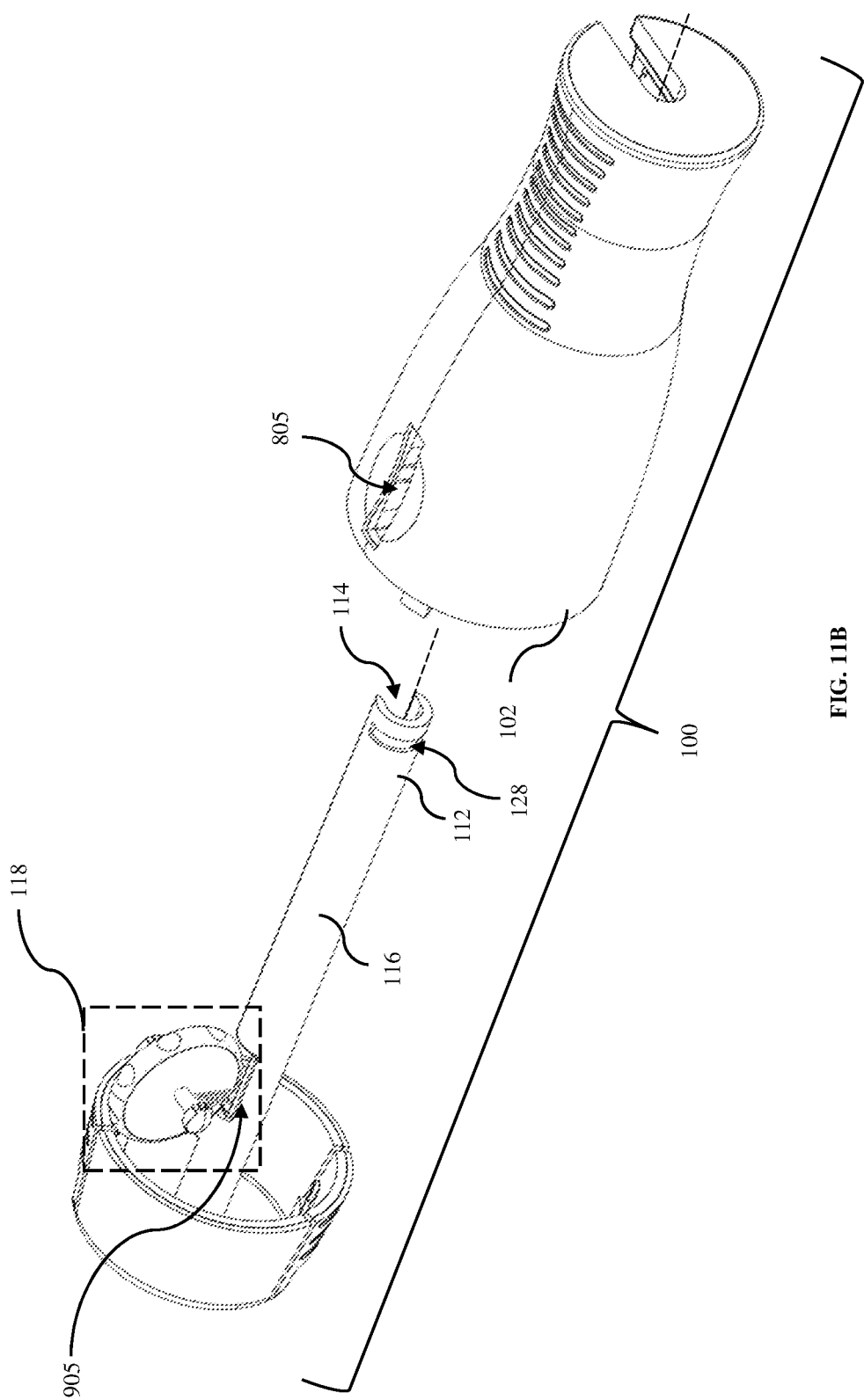

The first wheel 1005, prominently featured in FIGS. 10A through 10C, is a central component within the engaging element of the medical torquing device. The first wheel, thoughtfully incorporated within the slot of the engaging element, is a cylindrical shape with a central axis that allows it to rotate smoothly within the slot. The outer surface of the wheel is typically textured or ridged, and may include a plurality of ridges 1010, to facilitate a secure grip and precise manipulation by the operator. A ridge is a raised narrow elongated elevation or protuberance that forms a linear or curved line on the surface of an object. It is essentially a long, thin, and slightly elevated portion that contrasts with the surrounding surface. This textured surface ensures that the operator can easily rotate the wheel with their finger or thumb, and/or operatively scroll between configurations.

The second wheel 1015 is a critical component of the engaging element within the medical torquing device, as illustrated in FIGS. 10A through 10C. This cylindrical component features a unique design to facilitate controlled movements and precise locking and unlocking of the device during medical procedures. The second wheel 1015 is intimately connected to the first wheel 1005. It is attached to the first wheel in a manner that allows for synchronized movement. This attachment enables the operator to control both wheels simultaneously, ensuring smooth transitions between the locked and unlocked configurations of the device. It is understood that the engaging element may comprise at least one second wheel, and as depicted, there are two such wheels. These second wheels are designed to work in unison, serving as integral components of the engaging element. This dual-wheel configuration provides enhanced control and stability to the medical torquing device's locking and unlocking mechanism. It allows for precise and reliable manipulation, ensuring that the device can effectively secure and release medical instruments as required during various medical procedures. The coordinated action of these second wheels contributes to the overall functionality and versatility of the device.

In the described embodiment, the second wheel is attached to the first wheel using a cylindrical shaft that acts as a spacer 1030. The cylindrical shaft extends between the first and second wheels, creating a gap between them. This gap allows the second wheel to be properly positioned within the slotted channel of the engaging element. The cylindrical shaft serves as a connecting element between the two wheels, ensuring that they rotate together when the operator applies rotational force to the engaging element. As a result, the second wheel, with its teethed portion, can engage with the teeth on the walls of the slotted channel to lock the device securely in the desired configuration.

Within the slotted channel of the engaging element, the second wheel 1015 is strategically disposed. The second wheel 1015 features both teethed 1020 and non-teethed portions 1025, which play a crucial role in the locking and unlocking mechanisms.

When the operator manipulates the first wheel 1005, it, in turn, rotates the second wheel 1015 within the slotted channel. The interaction of the teethed portions of the second wheel with the teethed walls of the channel allows for precise control over the device's configuration. This synchronized movement of the wheels ensures that the engaging element functions effectively, securing or releasing the medical instrument as needed during procedures.

The biasing element 720, shown in FIGS. 7A and 7B, within the medical torquing device plays a critical role in its functionality. It is designed to apply an upward force on at least one second wheel, which is an integral part of the engaging element's mechanism. The biasing element ensures that the engaging element remains responsive and adaptable to the operator's actions, enhancing the overall user experience and control.

The biasing element's function is to exert a force that opposes the downward pressure applied by the operator on the engaging element. A biasing element, in the context of mechanical systems like the medical torquing device, is a component designed to exert a force that opposes certain movements or actions. It is used to provide resistance or assist in specific functions within the device. Biasing elements are commonly used in various mechanical systems to control movements, apply pressure, or maintain equilibrium, depending on the specific application and design requirements. They play a crucial role in achieving the desired functionality and user experience in such systems. The biasing elements employed in the medical torquing device can take various forms, each designed to fulfill the task of applying an upward force on the second wheel(s) within the engaging element. One common example is a coil spring, strategically positioned to exert consistent pressure. Alternatively, elastomeric elements, such as rubber or silicone components, can be utilized to provide the required upward force while also offering some flexibility in the application. Another option includes torsion springs, known for their rotational resistance and ability to maintain force in confined spaces. These biasing elements collectively ensure that the engaging element functions as intended, promoting smooth transitions between locked and unlocked configurations, ultimately enhancing the device's precision and usability during medical procedures.

By applying an upward force on the second wheel, the biasing element helps maintain a delicate balance in the system. This balance is essential, as it allows the operator to precisely control the engagement and disengagement of the device's locking mechanism. When the operator initiates the process of configuring the device into the locked or unlocked configuration, the biasing element's resistance ensures that the operator can feel and control the movement of the engaging element. This resistance provides tactile feedback, aiding in the smooth transition between configurations and the secure locking of the medical instrument in place.

Figure 6A:
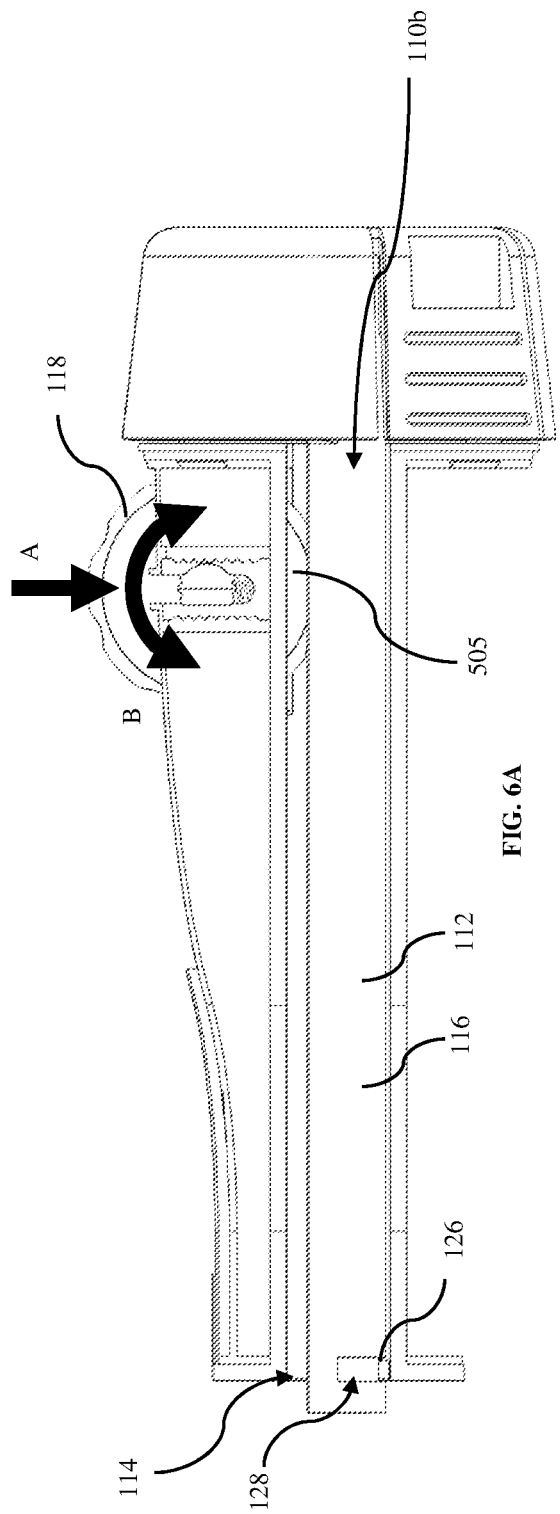
FIG. 6A is a side view of the medical torquing device depicting the medical torquing device in the closed and unlocked configuration, according to an example embodiment.

In FIG. 6A, the initial step in configuring the medical torquing device into the locked configuration is shown. Here, the operator applies a downward force, in the direction denoted by arrow A, on the first wheel 1005, denoted in FIG. 6A, while simultaneously initiating a rotation of the first wheel, in a direction denoted by arrow B. This combination of actions is pivotal for engaging the locking mechanism of the device. The application of a downward force on the first wheel 1005 is a deliberate action that serves to introduce the engaging element into the inner portion of the first u-channel, as previously explained. This downward movement of the engaging element is crucial for impeding the movement of the medical instrument, ensuring that it remains securely in place within the device.

Simultaneously, as the operator initiates the rotation of the first wheel, it begins to interact with the slotted channel's teethed walls, as discussed earlier. This rotation is instrumental in locking the engaging element in position, firmly securing the medical instrument in place within the device.

Figure 6B:
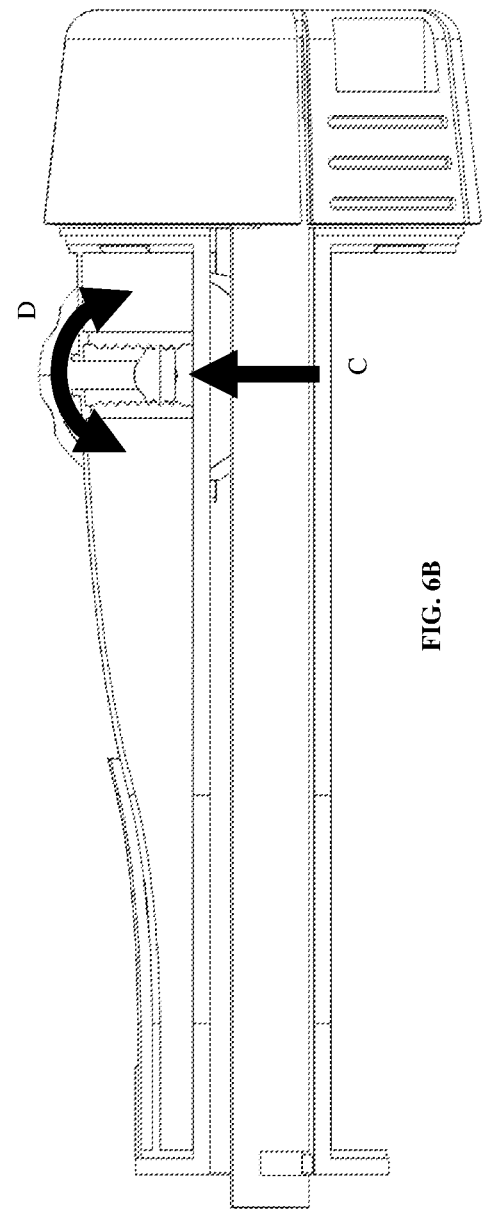
FIG. 6B is a side view of the medical torquing device depicting the medical torquing device in the closed and locked configuration, according to an example embodiment.

FIG. 6B, the subsequent illustration, showcases the result of these coordinated actions. In this configuration, the engaging element, comprising the first wheel 1005 and its associated components, is securely positioned within the inner portion of the first u-channel. This effectively locks the device, preventing any unintended movement of the medical instrument during procedures. As shown, the biasing element applies an upward force on the engaging element, as indicated by arrow C. This upward force helps maintain the engaging element in its locked position, ensuring that it securely retains the medical instrument within the device during medical procedures.

To release the engaging element from the locked configuration, a force denoted by the directions of arrow D must be applied to the engaging element. This force can be achieved by either rotating or sliding the engaging element, causing the non-teethed portion of the second wheel of the engaging element to be positioned proximate to the teethed portion of the slotted channel. This reconfiguration allows the engaging element to translate vertically, facilitating the release of the locked configuration and enabling the operator to adjust the medical instrument as needed during medical procedures.

In FIGS. 6A and 6B, a portion of the engaging element positioned within the inner portion of the u-channel is shown. This strategic placement restricts the movement of the medical instrument when the device is in the locked configuration, as shown in FIG. 6B. Additionally, it is noteworthy that when the handle is rotated to partially enclose the u-channel with the semi-tubular shaft, the open portion 114 of the shaft 112 is oriented upwards towards the engaging element 118. This specific orientation ensures that there is ample access for the engaging element to enter the inner portion of the u-channel, allowing it to effectively impede the movement of the medical instrument and secure it within the device when needed.

In FIG. 7A through 7C, a detailed view of the engaging element in the medical torquing device is shown, illustrating the stepwise process of transitioning between the unlocked and locked configurations. In FIG. 7A, a detailed view of the engaging element within the medical torquing device is shown, specifically highlighting the unlocked configuration in accordance with an example embodiment. Within this configuration, the engaging element, often referred to as a wheel, possesses the capability to translate in directions denoted by arrow A, which corresponds to vertical movement, allowing for precise control over its position. As part of this movement, a section of the engaging element, or a portion of the wheel, has entered into the inner portion of the u-channel. This strategic positioning restricts the movement of any medical instrument within the device, offering the operator the ability to finely adjust and secure the medical instrument's placement during various medical procedures. The unlocked configuration provides the necessary flexibility for instrument manipulation, making it a crucial feature for precise medical interventions and momentary movement restriction.

The portion of the wheel, in the context of the medical torquing device refers to a specific segment or section of the wheel, typically the lower part or a designated area of the wheel, that enters the first channel to inhibit the movement of the medical instrument. This portion is involved in engaging with the inner portion of the u-channel, creating an obstruction to secure the medical instrument within the device during use. This particular portion of the wheel aligns with the inner portion of the u-channel, creating an obstruction within the channel. When this engagement occurs, it effectively inhibits the movement of the medical instrument. This configuration ensures that the medical instrument remains securely positioned within the u-channel and prevents unintended displacement during medical procedures. The wheel's engagement with the inner portion of the u-channel can be controlled by the operator, allowing for precise adjustments and ensuring the medical instrument's stability within the device.

In the unlocked configuration, it is important to note that the non-teethed portion of the second wheel is positioned in close proximity to the plurality of teeth located on the slotted walls of the device. The term "proximate" refers to being near or in close proximity to something, indicating a close spatial or temporal relationship between two objects or concepts. In the context described, it means that the non-teethed portion of the second wheel is located closely or adjacent to the plurality of teeth on the slotted walls of the device without directly engaging with them. This arrangement allows for controlled and smooth movement of the engaging element, ensuring that the non-teethed portion does not engage with the teeth on the slotted walls. As a result, the medical instrument, such as a guidewire or catheter, can be easily maneuvered within the device, enabling precise adjustments and facilitating medical procedures without encountering resistance from the teethed surfaces. This feature enhances the operator's control over the instrument, contributing to the device's overall functionality in the unlocked configuration.

In a particular example embodiment, it's worth mentioning that one of the non-teethed portions of the second wheel may exhibit a curved design. This curvature allows it to maintain contact with the walls of the slotted channel as it moves within, ensuring a smooth transition when engaging the teethed portion of the second wheel with the teeth located on the walls of the channel. This curved feature aids in the precise and controlled movement of the engaging element, facilitating the transition from the unlocked configuration to the locked configuration without abrupt or jerky actions, ultimately contributing to the device's ease of use and effectiveness during medical procedures.

In FIG. 7B, an intermediary stage in the transition between the unlocked and locked configurations of the engaging element is shown. The first wheel is undergoing a rotation indicated by arrow B, which, in turn, causes the second wheel to rotate as indicated by arrow C. This rotation of the second wheel is essential for the engagement of its teethed portion with the teeth along the walls of the slotted channel. Simultaneously, the biasing element within the system may be compressed or exerting force on the second wheel, contributing to the secure engagement of the teethed portion with the channel walls. This intermediary step demonstrates the dynamic and controlled movement of the engaging element during the locking process, ensuring that the device securely holds the medical instrument in place during medical procedures.

In FIG. 7C, the transition from the unlocked to the locked configuration of the medical torquing device is completed. The engaging element, which includes the first wheel and second wheel, has been rotated and translated to its fully locked position. The teethed portion of the second wheel engages firmly with the teeth on the walls of the slotted channel, preventing any further vertical movement of the engaging element within the channel. This engagement securely locks the engaging element in place within the u-channel. This configuration effectively restricts the movement of the medical instrument inside the inner portion of the u-channel, ensuring precise control and stability during medical procedures. To release the locked configuration and allow the medical instrument to move freely, an operator can apply a force in the opposite direction, as indicated by arrow D, to disengage the engaging element from the teethed walls of the slotted channel.

In one embodiment, the engaging element takes the form of a button with a spring-loaded design. When the operator depresses the button, it compresses the internal spring. Simultaneously, a series of interconnected levers and gears translate this downward movement into a lateral motion, engaging with a stop mechanism inside the device. This stop prevents any unintended movement of the medical instrument within the inner portion of the u-channel.

It is understood that the engaging element within the medical torquing device is designed to be versatile in its positioning and may be located at various points along the device, including the top, sides, proximal portion, middle portion, and distal portions, offering flexibility in operation and ergonomic handling.

In another configuration, the engaging element features a sliding mechanism with grooves and channels. As the operator slides this element, it engages with a protruding stop mechanism within the device. This interaction restricts the movement of the medical instrument by creating a physical barrier, ensuring precise control during medical procedures.

In another example embodiment, the engaging element may include a locking mechanism akin to the one often found in retractable tape measures. It employs a button that, when pressed, disengages a coiled spring. The energy stored in the spring is then employed to engage a ratcheting stop mechanism, effectively immobilizing the engaging element. As a result of this locking action, the medical instrument within the inner portion of the u-channel is securely held in place.

In another example embodiment, when the operator actuates the engaging element mechanism, it engages with a series of pawls and teeth within the device. This interaction prevents any movement of the medical instrument within the inner portion of the u-channel, providing stability and control.

In another example embodiment, the engaging element may incorporate a rotational wheel mechanism configured to allow the operator to adjust the diameter of the engaging element around the inner portion of the u-channel. By rotating the wheel in one direction, the diameter gradually decreases, effectively constricting and securing the medical instrument within the inner portion. Conversely, rotating the wheel in the opposite direction enlarges the diameter, facilitating the smooth insertion or removal of the medical instrument from the u-channel. This versatile design provides precise control over the degree of constriction or expansion, offering flexibility in accommodating various sizes of medical instruments.

In another example embodiment, the engaging element may incorporate a screw mechanism, where both the slot and/or slotted channel are cylindrical and/or threaded. When the engaging element is twisted, it exerts a precise and controlled downward force onto the medical instrument. The twisting of the engaging element may engage the biasing element to facilitate controlled pressure on the medical instrument and smooth mechanics. The twisting action not only controls the magnitude of this force but also regulates the vertical positioning of the portion of the engaging element within the inner portion of the channel. This dynamic adjustment permits the operator to finely tune the movement of the medical instrument, either restricting or allowing more freedom of movement as needed during a procedure.

In each of these embodiments, the engaging element itself serves as a stop within the inner portion of the u-channel. In this configuration, the engaging element is designed with a particular shape or extension that acts as a physical obstruction. When the operator engages this stop by applying a downward force and possibly a rotational or sliding action, it enters the inner portion and impedes the movement of the medical instrument within the u-channel. This stop prevents the medical instrument from freely translating or rotating, effectively locking it in place. Releasing the stop involves reversing the operator's actions, such as lifting the engaging element and possibly rotating or sliding it to a position that no longer obstructs the inner portion. This embodiment provides a simple and reliable means of securing the medical instrument within the u-channel, ensuring stability during medical procedures.

It is understood that the terms "stop" and "engaging element" may also be defined as a torque-locking mechanism. In this context, a "torque-locking mechanism" refers to a device or element that, when engaged, restricts or locks the rotation or torque applied to the medical instrument within the inner portion of the u-channel. This locking mechanism ensures that the medical instrument maintains its position or orientation during a medical procedure, preventing unintended rotation or movement. It may involve various components, such as teeth, ratcheting mechanisms, or frictional elements, which, when activated, create resistance to torque or rotational forces applied to the medical instrument.

The preceding description of the medical torquing device highlights its multifaceted capabilities, which can be harnessed in an array of medical procedures. Referring now to FIG. 12, the ensuing method 1200 outlines a non-limiting approach for using this device, accommodating flexibility in execution. These steps empower medical professionals to apply the device effectively, enhancing precision and control during diverse medical operations, all while ensuring patient safety and procedural success.

The steps described herein are not limited to the particular order of their disclosure. In certain embodiments, the steps of operating the medical torquing device may occur concurrently, simultaneously, independently, dependently, or in any other suitable manner, as determined by the specific implementation and requirements, and tailored to each procedure's unique requirements. Therefore, the specific arrangement and order of the steps should be interpreted as illustrative rather than limiting, and the disclosure encompasses all variations, modifications, and alternatives falling within the scope of the appended claims. This flexibility empowers healthcare professionals to enhance precision, control, and efficiency in manipulating medical instruments, prioritizing patient safety and procedure success.

In accordance with the disclosed embodiment, a method for operating the medical torquing device begins by preparing the device for use, step 1205. The initial step 1205 involves ensuring that the device is in the open configuration, with the semi-tubular shaft aligned with the first channel, more specifically the slot of the first u-channel, to provide access to the inner portion of the first u-channel.

Once the device is ready, at step 1210, the operator carefully inserts a medical instrument, such as a guidewire or catheter for example, into the first u-channel through the elongated slot. The open configuration of the device permits seamless insertion and removal of the medical instrument, allowing for precise positioning.

As the operator proceeds with the procedure, the next step, step 1215, is to transition the device into the closed configuration. This is achieved by gradually rotating the handle or engaging the device's mechanism, causing the semi-tubular shaft to partially enclose the first u-channel. This movement facilitates controlled manipulation of the medical instrument within the inner portion of the u-channel.

Since the medical instrument is secured in the medical torquing device, the operator can proceed with the procedure. In step 1220, the operator may position the medical instrument which may involves the manual advancement of the medical instrument within the inner portion of the device. The operator, typically holding the medical torquing device with one hand, which in turn supports the medical instrument, utilizes their other hand to apply controlled pressure to the medical instrument. This pressure is directed to pass or feed the medical instrument through the inner portion of the device, thereby further advancing it within the patient's anatomy during the medical procedure. This step is essential for precise control and adjustment of the instrument's position within the patient's body, ensuring the effectiveness and accuracy of the medical intervention. It's worth noting that the device's design facilitates this manual positioning process, allowing for seamless and controlled movement of the medical instrument within the inner portion, ultimately contributing to the success of the medical procedure.

To secure the medical instrument in place, the operator has the option of engaging the torque locking mechanism, also referred to as the engaging element, at step 1225. This engagement can take two forms. In the first, a downward force is applied to the engaging element, permitting a portion of it to enter the inner portion and provide momentary control over the instrument's movement. In the second, a double-action engagement is performed, where a downward force is applied while simultaneously rotating or sliding the engaging element. This action securely locks the engaging element within the inner portion, ensuring that the medical instrument remains in a fixed position.

Should the need arise to unlock the device, the operator can initiate the unlocking process, step 1230, by either reversing the double-action engagement or applying a vertical force to the engaging element. When applying a downward force alone, the operator effectively lightens the pressure on the engaging element, allowing the biasing elements, typically springs, to come into play. These biasing elements apply an upward force, smoothly transitioning from inhibiting the motion of the medical instrument to permitting it to move freely within the u-channel. Alternatively, if the double-action engagement was initially employed to firmly fix the device in the locked configuration, releasing this locked state can be achieved by applying a reverse force. This force can take various forms, such as a press, slide, or scroll, depending on the specific implementation and design of the engaging element. Regardless of the method chosen, the operator can easily and efficiently switch between locked and unlocked configurations, ensuring precise control over the medical instrument's movement during the medical procedure.

For instrument removal, step 1235, the operator transitions the device back into the open configuration by adjusting the handle or the mechanism accordingly. This aligns the open portion of the semi-tubular shaft with the elongated slot, facilitating the controlled and precise removal of the medical instrument.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A medical device system comprising:
    an elongated outer body having a length greater than a width, the elongated outer body comprising a longitudinal axis parallel to the length, an outer circumferential surface extending the length of the elongated outer body and around the longitudinal axis, a proximal end face, and a distal end face;

a first u-channel spanning the length of the elongated outer body from the proximal end face through the distal end face and wherein the first u-channel extends radially outward from the longitudinal axis to the outer circumferential surface defining a contiguous opening on the proximal end face, the outer circumferential surface, and the distal end face;

a semi-tubular shaft comprising an open portion and a closed portion, the semi-tubular shaft disposed within the first u-channel of the elongated outer body;

a closed configuration comprising the closed portion of the semi-tubular shaft covering at least a portion of the first u-channel;

an open configuration comprising the open portion of the semi-tubular shaft being at least partially aligned with the first u-channel; and an engaging element comprising a locked configuration and an unlocked configuration;

wherein, in the locked configuration, at least a portion of the engaging element is disposed in the first u-channel.

2. The medical device system of claim 1, wherein the first u-channel further comprises:

an elongated slot contiguous to an inner portion, wherein the semi-tubular shaft is disposed within the inner portion.

3. The medical device system of claim 2 further comprising a handle attached to an end portion of the semi-tubular shaft, the handle comprising a second u-channel.

4. The medical device system of claim 3, the engaging element further comprising:

a second slot on the outer circumferential surface of the elongated outer body wherein the second slot is contiguous to the inner portion of the first u-channel;

a slotted channel intersecting with and perpendicular to the second slot, the slotted channel comprising a first channel wall opposing a second channel wall;

a plurality of teeth extending along each of the first channel wall and the second channel wall;

a first wheel disposed within the second slot;

at least one second wheel attached to the first wheel and disposed within the slotted channel, wherein the at least one second wheel comprises a teethed portion on a first side of the at least one second wheel and a non-teethed portion on an opposing side of the at least one second wheel; and at least one biasing element configured to apply an upward force on the at least one second wheel.

5. The medical device system of claim 4, wherein the locked configuration further comprises the teethed portion of the at least one second wheel engaging with the plurality of teeth on each of the first channel wall and the second channel wall.

6. The medical device system of claim 5, wherein the unlocked configuration comprises the teethed portion of the at least one second wheel not engaging with the slotted channel such that the non-teethed portion is disposed proximate to the plurality of teeth on each of the first channel wall and the second channel wall thereby allowing controlled upward and downward movement of said first wheel within said slotted channel.

7. The medical device system of claim 6, the semi-tubular shaft further comprising an opening proximate to the second slot in the elongated outer body, and wherein the locked configuration further comprises a portion of the first wheel extending through the open portion of the semi-tubular shaft such that the portion of the first wheel is disposed within the first u-channel.

8. The medical device system of claim 6 wherein the inner portion of the first u-channel comprises a detent and wherein the semi-tubular shaft comprises a keyway configured to operatively engage with the detent.

9. A medical torquing device system comprising:

an elongated outer body having a length greater than a width, the elongated outer body comprising a longitudinal axis parallel to the length, an outer circumferential surface extending the length of the elongated outer body and around the longitudinal axis, a proximal end face, and a distal end face;

a first channel spanning the length of the elongated outer body from the proximal end face to through the distal end face;

a stop comprising a locked configuration and an unlocked configuration;

a second slot on the outer circumferential surface of the elongated outer body wherein the second slot is contiguous to an inner portion of the first channel;

a slotted channel intersecting with and perpendicular to the second slot, the slotted channel comprising a first u-channel wall opposing a second channel wall;

a plurality of teeth extending along each of the first channel wall and the second channel wall;

a first wheel disposed within the second slot;

at least one second wheel attached to the first wheel and disposed within the slotted channel, wherein the at least one second wheel comprises a teethed portion on a first side of the at least one second wheel and a non-teethed portion on an opposing side of the at least one second wheel; and at least one biasing element configured to apply an upward force on the at least one second wheel.

10. The medical torquing device system of claim 9 further comprising:

a shaft comprising an open portion and a closed portion, the shaft disposed and rotatable within the first channel of the elongated outer body; and a handle attached to an end portion of the shaft, the handle comprising a second channel and a second closed portion.

11. The medical torquing device system of claim 10, wherein the first channel further comprises an elongated slot contiguous to an inner portion, wherein the shaft is disposed within the inner portion.

12. The medical torquing device system of claim 10, further comprising a closed configuration comprising the closed portion of the shaft covering at least a portion of the first channel and configured to operatively retain a medical instrument within the first channel.

13. The medical torquing device system of claim 10 wherein the first channel u-channel comprises a detent and wherein the shaft comprises a keyway configured to operatively engage with the detent.

14. The medical torquing device system of claim 9, wherein in the locked configuration at least a portion of the stop is disposed in the first channel.

15. The medical torquing device system of claim 9 wherein the stop is a double-action engaging element operable by an operator to apply a downward force and concurrently engage in rotational movement to transition the medical torquing device system between the locked configuration, inhibiting a movement of a medical instrument within the first channel, and the unlocked configuration, permitting the medical instrument to freely move within the first channel.

16. The medical torquing device system of claim 9 wherein the stop comprises a first wheel in attachment with at least one second wheel, the at least one second wheel comprising a teethed portion, a first non-teethed portion, and a second non-teethed portion comprising a curvature.

17. The medical torquing device system of claim 9 wherein the stop is a handle, wherein in the unlocked configuration, the handle is configured to receive a medical instrument within the first channel, and wherein in the locked configuration, the handle is configured to retain the medical instrument within the first channel.

18. A medical torquing device system for one-handed operation to facilitate control over a medical instrument's positioning and rotational torque, the medical torquing device system comprising:

an elongated outer body having a length greater than a width, the elongated outer body comprising a longitudinal axis parallel to the length, an outer circumferential surface extending the length of the elongated outer body and around the longitudinal axis, a proximal end face, and a distal end face;

a first channel spanning the length of the elongated outer body from the proximal end face through the distal end face; and a stop comprising a locked configuration and an unlocked configuration;

wherein in the locked configuration at least a portion of the stop is disposed in the first channel.

19. The medical torquing device system of claim 18 wherein the stop comprises a first wheel in attachment with at least one second wheel, the at least one second wheel comprising a teethed portion, a first non-teethed portion, and a second non-teethed portion comprising a curvature.

20. The medical torquing device system of claim 19 wherein the stop is a double-action engaging element operable by an operator to apply a downward force and concurrently engage in rotational movement to transition the medical torquing device system between the locked configuration, inhibiting a movement of a medical instrument within the first channel, and the unlocked configuration, permitting the medical instrument to freely move within the first channel.

\* \* \* \* \*